United States Patent [19]

Bickel et al.

[11] 4,005,077

[45] Jan. 25, 1977

[54] ANTIBIOTICALLY ACTIVE COMPOUNDS

[75] Inventors: Hans Bickel, Binningen; Wilhelm Kump, Biel-Benken, both of Switzerland

[73] Assignee: Ciba-Geigy Corporation, Ardsley, N.Y.

[22] Filed: Sept. 25, 1974

[21] Appl. No.: 508,974

Related U.S. Application Data

[63] Continuation-in-part of Ser. No. 342,222, March 16, 1973, abandoned, which is a continuation-in-part of Ser. No. 5,899, Jan. 26, 1970, abandoned, which is a continuation-in-part of Ser. No. 571,413, Aug. 10, 1966, abandoned.

[30] Foreign Application Priority Data

Aug. 24, 1965 Switzerland .................... 11879/65
Aug. 11, 1969 Switzerland .................... 12131/69
Dec. 8, 1969 Switzerland .................... 18249/69

[52] U.S. Cl. ........................ 260/239.3 P; 424/250; 424/244
[51] Int. Cl.² ........................................ C07D 491/06
[58] Field of Search ........................ 260/239, 3 P

*Primary Examiner*—Henry R. Jiles
*Assistant Examiner*—Robert T. Bond
*Attorney, Agent, or Firm*—Joseph G. Kolodny; John J. Maitner; Theodore O. Groeger

[57] ABSTRACT

Antibiotically active compounds derived from rifamycin S or from the corresponding hydroquinone, rifamycin SV, or from derivatives at least partially hydrogenated in positions 16, 17; 18, 19; 28, 29, such as the 16, 17; 18, 19 - tetrahydro- or the 16, 17; 18, 19; 28, 29 - hexahydro derivatives, which contain in position 3 a free or an aliphatically substituted amino group. The hydrocarbon radicals of the aliphatically substituted amino group can also be interrupted in their carbon chain by heteroatoms and/or be substituted by functional groups.

A special group of these new compounds is represented by 3-amino derivatives as defined above, in which the amino group is a particular type of N- aza - cyclo - aliphatic radical unsubstituted by functional groups, and which has, in addition to the antibiotic action against sensitive microorganisms also an antibacterial activity against certain types of resistant microorganisms.

Another special group is represented by 3- amino derivatives as defined above, in which the amino group is a particular type of a 4R - 1 - piperazinyl radical, in which R is a hydrocarbon radical ; they have a special high antituberculosis action, while having very low toxicity.

10 Claims, No Drawings

ANTIBIOTICALLY ACTIVE COMPOUNDS

CROSS REFERENCE TO RELATED APPLICATIONS

This is a continuation-in-part - in - part of application Ser. No. 342,222, filed Mar. 16, 1973, now abandoned which is, in turn, a continuation in part of application Ser. No. 5,899, filed Jan. 26, 1970, now abandoned which is, in turn, a continuation in part of application Ser. No. 571,413, filed Aug. 10, 1966, now abandoned.

SUMMARY OF THE INVENTION

The present invention relates to the manufacture of new antibiotically active compounds, derived from rifamycin S, of the following formula

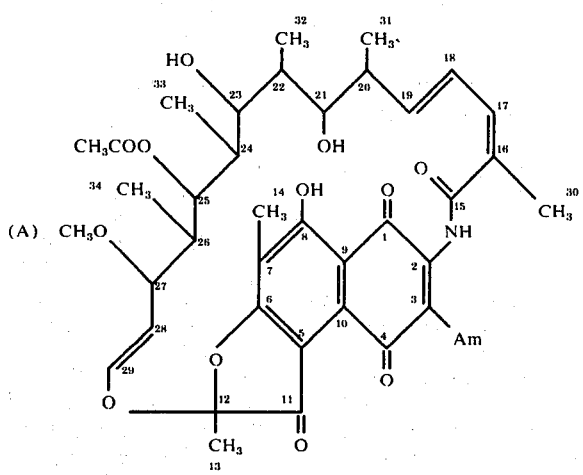

and their corresponding hydroquinones, derived frm rifamycin SV, and to their derivatives at least partially hydrogenated in positions 16, 17; 18, 19; 28, 29, especially the 16, 17; 18, 19 - tetrahydro- or the 16, 17; 18, 19; 28, 29 - hexahydro derivatives, Am representing in the above formula a primary amino group or a secondary or tertiary amino group aliphatically linked at the nitrogen atom of the amino group, and therapeutically acceptable metal salts of compounds having acidic character, therapeutically acceptable acid addition salts of compounds having a basic group, and quaternary ammonium salts thereof.

SPECIFIC EMBODIMENTS OF THE INVENTION

The above 3-amino group of the rifamycin S or SV compounds or their derivatives at least partially hydrogenated in the rifamycin side chain is aliphatically linked by the substituting hydrocarbon radicals or their substituted derivatives at the nitrogen atom, which means that these hydrocarbon radicals have aliphatic character, that is to say they are hydrocarbon radicals or their substituted derivatives, whose first carbon atom linked with the nitrogen atom is not a member of an aromatic system. Such an amino group has the characteristics of the aliphatic or araliphatic amines or of the azacyclic bases whose ring is not aromatic, as for instance in the case of pyrrolidine or piperidine or their derivatives.

A secondary or tertiary amino group present in 3-position of the rifamycin moiety as defined above correspond to either of the formulae

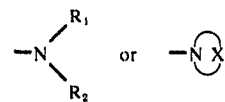

wherein the groups $R_1$ and $R_2$ are monovalent hydrocarbon radicals aliphatically linked at the nitrogen atom, or hydrogen, at least one of these groups being one of the said radicals aliphatically linked at the nitrogen atom, and X is a divalent hydrocarbon radical aliphatically linked at the nitrogen atom, which hydrocarbon radicals may also be interrupted in the carbon chain by hetero atoms, such as nitroen, oxygen or sulphur atoms and/or may be substituted by one, two or more identical or different functional groups, such as free or etherified hydroxyl groups, halogen atoms, free or esterified carboxyl or sulphonic acid groups, aldehyde groups, nitrile groups or amino groups.

Monovalent hydrocarbon radicals $R_1$ or $R_2$ as defined above are e.g. alkyl groups or their unsaturated derivatives, especially alkenyl groups, cycloalkyl groups or their unsaturated derivatives, especially cycloalkenyl groups, cycloalkyl - alkyl groups or their unsaturated derivatives, especially cycloalkenyl - alkyl or cycloalkyl - alkenyl radicals, or phenylated derivatives of all these radicals, and the derivatives of all these radicals interrupted in the carbon chain by heteroatoms and/or substituted, as said above, by functional groups or their derivatives. A divalent radical X as defined above is e.g. an alkylene group with straight or branched carbon chain, which may also be substituted in the same manner as said for the monovalent radicals, e.g. by phenyl or cycloalkyl groups or by the functional substituents mentioned, and can be interrupted in the carbon chain by heteroatoms, as said above, or an unsaturated derivative of such alkylene, phenylalkylenes or cycloalkylalkylene radicals or their substituted derivatives. The amino group formed by such alkylene groups or their derivatives, substituting the amino nitrogen atom can also be defined as N-aza cyclo - aliphatic hydrocarbon radicals, optionally interrupted in the carbon chain by one or more of the said hetero - atoms and/or substituted by one or more of the said functional groups or their derivatives. Such N- azacyclo - aliphatic hydrocarbon radicals can also be saturated or unsaturated, in particular mono- unsaturated.

The hydrocarbon radicals X or $R_1$ together with $R_2$ contain advantageously not more than 20 carbon atoms. X, $R_1$ and $R_2$ taken individually have preferably no more than 12 carbon atoms, they have especially no more than 8 carbon atoms.

The groups $R_1$ or $R_2$ are in particular lower alkyl groups of 1 to 8 carbon atoms, such as methyl, ethyl, propyl, isopropyl, linear or branched butyl, pentyl, hexyl or heptyl groups, which may be linked in any desired position with the N- atom of the 3-amino group. Alkenyl groups also preferably have 1 to 8 carbon atoms, such as the allyl or methallyl group. Lower alkylene groups having 2–8 carbon atoms are for instance ethylene-(1,2), butylene-(1,4), pentylene-(1,5), hexylene-(1,6), hexylene-(1,5), hexylene-(2,5), heptylene-(1,7), heptylene-(2,7) or heptylene-(2,6). Lower cycloalkyl or cycloalkyl - alkyl radicals or their unsaturated derivatives having from 3–8 carbon atoms in the ring and 1–8 carbon atoms in the aliphatic moiety are for instance cyclopentyl, cyclohexyl, cyclopentylmethyl, cyclopentylethyl, cyclohexylmethyl, cyclohexylethyl, cyclohexenyl- or cyclopentenyl methyl - or ethyl or cyclohexeneyl - methyl - or - ethyl.

The bivalent radicals X of the alkylene type mentioned forms with the nitrogen atom of the 3-amino group in the rifamycin moiety an N-azacycloalkyl group. Thus, for instance, if the said nitrogen atom is substituted by the butylene-(1,4)- radical, the azacycloalkyl group formed is a pyrrolidino radical and if it is substituted by the pentylene-(1,5)-radical or the hexylene-(2,5)-radical, the azacycloalkyl group formed is a piperidino and a 2,5-dimethyl-pyrrolidino radical respectively etc.

Numerous further examples of such amino groups will be given below.

The group

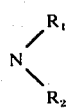

may especially be a mono- or -dialkyl amino group, wherein the alkyl groups have 1 to 4 carbon atoms, such as the monomethylamino, dimethylamino, monoethylamino, diethylamino, monopropyl, dipropyl, mono-isopropyl or di-isopropyl or mono- or di-butylamino groups.

Among the phenylated derivatives of lower alkyl groups there are especially to be mentioned phenyl - lower alkyl groups having 1 to 8 carbon atoms in the alkyl moiety in which the phenyl radical may be unsubstituted or contains, one, two or more identical or different substituents, such as a lower alkyl or lower alkoxy groups having 1 to 3-carbon atoms, halogen atoms or carboxyl groups, such as benzyl, para- chlorobenzyl, para - methoxybenzyl, 1-phenylethyl and 2-phenylethyl group.

Radicals $R_1$, $R_2$, X as defined above which are interrupted in the carbon chain by heteroatoms such as nitrogen, oxygen or sulphur atoms, are for example mono- or poly-aza-alkyl-, -azaalkylene-, -oxaalkyl-, -oxaalkylene-, -thiaalkyl-, -thiaalkylene, aza-, oxa or thia - cycloalkyl - alkyl radicals, or radicals of this type containing different hetero atoms, such as oxaaza - alkyl or oxaazacycloalkyl - alkyl radicals.

Azaalkyl or azacycloalkyl - alkyl radicals, particularly mono - aza - radicals of this type of value are those derived from the above said alkyl groups having from 1 to 8 carbon atoms or from cycloalkyl - alkyl radicals having from 3 to 8 ring carbon atoms and 1 to 8 carbon atoms in the aliphatic moiety such as propyl, isopropyl, linear or branched butyl, pentyl, hexyl or heptyl groups interrupted at any position in the carbon chain or in the ring by nitrogen atoms. Such groups are thus for instance an aliphatic hydrocarbon radical which carries an amino group, especially a tertiary amino group, such as for instance a di- lower alkylaminoethyl, di- lower alkylaminopropyl or di- lower akylaminobutyl group. Thus, the substituent in position 3 of the rifamycin moiety is, e.g. a dimethylamino-ethylamino-, a diethylamino-ethylamino, a diisopropylaminoethylamino-, a dipropylamino - ethylamino, a dimethylamino - propylamino or a diethylamino - propylamino group.

Among the azaalkylene radicals there are especially to be mentioned those which together with the amino nitrogen atom in the 3-position of the rifamycin moiety form a diazacycloalkyl ring containing 6 to 9 ring members, in which the nitrogen atoms are separated by at least 2 carbon atoms. The diazacycloalkyl ring may be substituted on the carbon atoms by one, two or more identical or different lower alkyl groups having from 1 to 6 carbon atoms, preferably by methyl or ethyl groups and/or on the N'-nitrogen atom for example by lower alkyl or hydroxy alkyl radicals having from 1 to 6 carbon atoms, such as methyl, ethyl, propyl or isopropyl, linear or branched butyl, pentyl or hexyl radicals, which may be linked in any desired position, or by β-hydroxyalkyl groups, such as β-hydroxyethyl or β,γ-dihydroxypropyl groups, by lower alkoxyalkyl groups such as methoxy - or ethoxy - ethyl or - propyl groups, by carbalkoxy groups or by phenyl or phenyl - lower alkyl groups, such as benzyl - or (1) or (2) - phenethyl radicals which may be substituted in the aromatic rings by one, two or more identical or different radicals or functions, for example alkyl or alkoxy groups and/or halogen atoms, the term alkyl indicating groups have 1 to 6 carbon atoms. The diazacycloalkyl ring is above all a piperazino group which may be substituted as indicated above, being more especially a methyl, ethyl- or β-hydroxyethyl piperazino group.

The above mentioned azaalkyl radical may also be formed by an alkyl group which carries, instead of the said di - lower alkylamino group, a pyrrolidino-, a piperidino, a morpholino- or piperazino group, whose rings may also be substituted, as said above for the N'-atom of the diazacycloalkyl group. Such radicals are for instance a pyrrolidino-, a piperidino-, a morpholino- or a piperazino-lower alkyl group having from 1 to 8 carbon atoms in the alkyl moiety, e.g. an ethyl-, propyl-, or butyl group. The substituent in the 3-position of the rifamycin moiety is thus for instance or pyrrolidino - ethylamino-, a morpholino - propylamino - or an N'-methyl - piperazino - ethylamino group. The last named types represent thus the case in which the substituting radicals at the nitrogen atom in 3-position of the rifamycin moiety aliphatically linked as said above, are interrupted by more than one hetero atoms in the carbon chain, that is to say they are diazaalkyl and oxazaalkyl radicals.

The functions which may substitute the radicals mentioned may be free hydroxyl groups, etherified hydroxyl groups, such as lower alkoxy groups having 1 to 4 carbon atoms, such as methoxy, ethoxy, propoxy or butoxy groups, free or esterified carboxyl groups, especially carboxyl groups esterified with lower aliphatic alcohols having 1 to 4 carbon atoms, such as carbethoxy groups, sulphonic acid groups, aldehyde groups, nitrile groups or amino groups. The amino groups are preferably those mentioned above, such as a dialkylamino group or the cyclic amino groups, such as those derived from pyrrolidino, piperidino, piperazino, morpholino or their alkylated derivatives, especially the methylated derivatives.

Among the 3-amino groups with hydrocarbon radicals as defined which are substituted by the functional groups mentioned above are to be set forth especially, besides, the diamines mentioned above, such as the dimethyl- or diethylamino - ethylamino group, alkylamino or alkyleneamino groups substituted by free or etherified hydroxyl groups, especially lower alkoxy groups with 1 to 4 carbon atoms, especially such alkylamino or alkyleneamino groups having from 1 to 8 carbon atoms, such as for instance mono- or poly-hydroxy or lower alkoxy monoalkyl- or dialkyl- amino groups having 1 to 8 carbon atoms in the alkyl group, and mono- or polyhydroxy or lower alkoxyalkyleneamino groups having from 2 to 8 carbon atoms and especially 5–7 ring carbon atoms, such as, for instance, 3-hydroxy - pyrrolidino, 3-hydroxy - piperidino, 4-hydroxypiperidino, 3,4- or 5- hydroxy - azepino groups, or the corresponding derivatives having an alkoxy or ethoxy group instead of the hydroxy group.

The new 3-amino rifamycin derivatives can be prepared and used in the quinonic form (3-amino rifamycin S derivatives) and the hydroquinonic form (3-amino rifamycin SV derivatives). Both forms are easily converted into another. The compounds may also be present in the form of their tautomers.

Most of the new 3-aminoquinones are crystalline compounds of violet red colour; they are insoluble in water, but readily soluble in most organic solvents, such as alcohols, halogenated hydrocarbons, esters, dioxane and the like. They can be reduced by reducing agents, for example hydrogen sulphite, dithionite or especially ascorbic acid or its salts to form yellow-coloured, generally likewise crystalline hydroquinones. The hydroquinones from metal salts, e.g. alkali metal salts, especially in the case when the 3-amino substituent does not carry any other basic group, and the aqueous solutions of such alkali metal salts are of approximately neutral reaction. In an alkaline solution the hydroquinones are very readily transformed into the quinones, and the oxidation can also be brought about by the reagents which are usual for the hydroquinones such as ammonium persulfate, potassium ferricyanide, hydrogen peroxide or also merely by air. The sodium salts of the hydroquinone derivatives are preferably used.

The quinones may likewise be present in the form of their alkali metal salts, provided they carry acid groups on the 3-substituent. Quinones and hydroquinones that carry a basic group on the 3-substituent form with acids acid addition salts and possibly quaternary ammonium salts, especially with esters of alkanols having from 1 to 16 carbon atoms, and especially lower alkanols having from 1 to 8 carbon atoms, with hydrohalic acids such as hydrodic, hydrobromic or hydrochloric acid, sulphuric acid or sulphonic acids. To prepare acid addition salts there are used above all acids capable of forming therapeutically acceptable salts, for example hydrohalic acids, sulphuric and phosphoric acids, nitric and perchloric acid; aliphatic, alicyclic, aromatic or heterocyclic carboxylic or sulphonic acids such as formic, acetic, propionic, succinic, glycollic, lactic, malic, tartaric, citric, ascorbic, maleic, hydroxymaleic or pyruvic acid; phenylacetic, benzoic, para-aminobenzoic, anthranilic, para-hydroxy-benzoic, salicyclic or para-aminosalicyclic acid, embonic, methanesulphonic, ethanesulphonic, hydroxyethanesulphonic, ethylenesulphonic acid; halobenzenesulphonic, toluenesulphonic, naphthalenesulphonic acids or sulphanilic acid; methionine, trypthophan, lysine or arginine.

The afore-mentioned or other salts of the new compounds, for example their picrates, may also be used for purifying the resulting bases, by converting the bases into salts, isolating the salts and liberating the bases again from them. In view of the close relationship between the bases in the free form and in the form of their salts what has been said above and hereinafter with reference to the free bases concerns also the corresponding salts wherever this is possible and useful.

The new 3-amino rifamycins S and -SV mentioned above and their afore mentioned hydrogenation products are distinguished by a high antibiotic activity. Thus they are very potent antibacterial agents, for example, against gram positive bacteria, such as the staphlococci, as has been shown for example, in bacterial cultures in vitro. For instance, they possess in cultures of Staphylococcus aureus SG 511 in the serial dilution test a minimum inhibitory concentration in the range of about 0,0001 γ/ml to about 3 γ/ml. The antibiotic activity against these gram positive bacteria can also be shown in animal tests, for example, in mice. Furthermore, the new compounds of the present invention display in animal tests, for example in mice, an antitubercular activity. The new compounds are therefore useful for treating bacterial infections, especially tuberculosis. The new compounds are also valuable intermediates for the manufacture of other useful substances, especially of pharmacologically active compounds.

Special mention deserve 3-(N'-lower alkyl or N'-hydroxyalkyl)-piperazino-rifamycin S and SV, above all 3-(N'-methylpiperazino)-rifamycin S and SV; furthermore 3-cyclohexylamino-rifamycin SV, and 3-cyclopropylamino-rifamycin S and SV, 3-morpholino-rifamycin SV and 3-lower alkyl-amino-rifamycin S and SV, especially 3-methylamino-, 3-ethylamino- and 3-isopropylamino-rifamycin SV. The latter compound produces, for example on oral administration to mice in doses from 10 to 50 mg per kg bodyweight, a distinct tuberculostatic effect and the same result is achieved also with 3-morpholino-rifamycin SV. The antibacterial activity of 3-morpholino-rifamycin SV as determined in mice infected with staphylococci is by far superior to that of rifamycin SV.

Special mention also deserves a particular group of 3-amino - rifamycin S - and SV derivatives and their derivatives hydrogenated in at least one of the positions 16, 17; 18, 19; 28, 29: as defined above wherein the 3-amino group is an azacycloaliphatic radical with at least 3 ring carbon atoms and only tetragonal α-carbon atoms and, if it has fewer than 8 ring carbon atoms, additionally possesses a further carbon - to - carbon bond starting from at least one of the positions other than the α-positions. The compounds of this selected group exhibit in addition to the high antibiotic action as described above, such as a very good action against gram-positive microorganisms, an antibacterial action against rifampicin resistant staphylococci, and corresponding mutants of Mycobacterium tuberculosis. Rifampicin, that is to say 3- (4'-methyl-1'-piperazinyl-iminomethyl)-rifamycin SV is one of the most active rifamycin derivatives. The new 3-amino - rifamycin compounds of the selected group just mentioned show, at a selection concentration of 100 mcg/ml a 100 - fold lower mutation rate to resistance in the case of gram-positive microorganisms as compared to rifampicin.

In the compounds of this group of 3-amino - rifamycin S and SV derivatives which are active against the said rifampicin resistant microorganisms, the 3- azacycloaliphatic radical is one in which the aza- cycloaliphatic ring is saturated or unsaturated with at least three carbon atoms and preferably not more than 24 carbon atoms and which ring can be substituted by further aliphatic, cycloaliphatic aromtic or araliphatic hydrocarbon radicals. Aliphatic hydrocarbon substituents are for example alkyl groups, especially lower alkyl, lower alkenyl or lower alkylidene groups having 1 to 7 carbon atoms, or alternatively straight chain or branched, preferably lower, alkylene groups having from 2 to 7 carbon atoms, which can in turn be saturated or unsaturated, especially mono unsaturated, and link two carbon atoms of the aza- cycloaliphatic ring. In the latter case a polycyclic aza- cycloaliphatic radical is present, such as for example an aza- bicyclo - or aza-tricyclo - alkane. Such radicals can also be viewed as having been produced by linking two carbon atoms of a monocyclic aza-cycloaliphatic radical by means of an endo- carbon to -carbon bond. An alkylene radical, preferably a lower alkylene radical as said above, can however also substitute the 2-hydrogen atoms of the same carbon atoms of the aza- cycloaliphatic ring, whereby spiro- cyclic substituted derivatives are produced. Cycloaliphtic substituents are preferably cyclo-alkyl or cycloalkenyl groups with 3–8 ring carbon atoms, which in turn, can be substituted by alkyl, benzyl or phenyl or alkylene groups, that is to say in the latter instance represent bicyclic cycloaliphatic hydrocarbon radicals. Aromatic hydrocarbon radicals as substituents of the aza- cycloaliphatic ring may be monocyclic or polycyclic aryl radicals, especially a phenyl or naphthyl radical, which is unsubstituted or substituted by further hydrocarbon radicals such as alkyl groups, especially lower alkyl groups. Araliphatic radicals are preferably monocyclic aryl-lower aliphatic radicals, especially phenyl lower alkyl radicals. Aromatic nuclei can also be fused with the aza-cycloaliphatic ring.

As preferred substituents of the aza-cycloaliphatic rings which have been mentioned, the following may be quoted: monovalent or divalent aliphatic hydrocarbon radicals, primarily those with 1–7 carbon atoms, that is to say lower alkyl groups such as methyl, ethyl, straight or branched propyl, butyl or pentyl groups bonded in any desired position, lower alkenyl groups such as vinyl, allyl or methallyl groups or lower alkylene groups with at most 7 carbon atoms, for example methylene, ethylene, propylene, butylene or pentylene radicals or cycloaliphatic hydrocarbon radicals, preferably with 3–8 ring carbon atoms, such as cycloalkyl groups, for example cyclopentyl or cyclohexyl groups, or cycloaliphatic-aliphatic hydrocarbon radicals, preferably with 3–8 ring carbon atoms and at most 7 chain carbon atoms such as cycloalkyl-lower alkyl groups, for example cyclopentylmethyl, cyclohexylmethyl, cyclohexylpropyl or cyclohexylethyl groups, or aromatic, especially monocyclic or bicyclic hydrocarbon radicals, such as phenyl or naphthyl groups, and araliphatic hydrocarbon radicals such as phenyl- or naphthyl-lower alkyl groups, for example benzyl, phenylethyl, diphenylmethyl or naphthylmethyl groups.

The cycloaliphatic and aromatic hydrocarbon substituents or fused cycloaliphatic and aromatic rings can in turn be substituted, for example by lower alkyl groups, preferably with up to 7 carbon atoms.

In the aza- cycloaliphatic radical present in the 3-position of the 3-amino - rifamycin compounds mentioned pertaining to the selected group of compounds which are active against rifampicin resistant microorganisms no double bond may start from the αor α'-carbon atom because of the condition mentioned that these carbon atoms are tetragonal. Preferably the azacycloaliphatic radical possesses 3–11 ring carbon atoms. The above mentioned condition that a further carbon - to - carbon bond should be present in at least one of the positions other that the α- or α'-position of the aza- cycloaliphatic ring, provided this ring possesses fewer than 8 carbon atoms, means that in at least one of these positions one of the above - mentioned substituents is present or that an endo-carbon - to carbon bond or a ring - double bond starts from these positions.

The aza- cycloaliphatic radical in 3-position is in particular an alkyleneamino group having 3–11 ring carbon atoms or an unsaturated derivative thereof. Unsubstituted saturated alkyleneamino groups must have more than 9 ring carbon atoms.

The alkyleneamino group is thus for example an azetidin-1-yl, pyrrolidino, piperidino, hexahydroazepin-1-yl, octahydroazocin-1-yl, octahydroazocin-1-yl, decahydroazecin-1-yl, aza- cycloundec-1-yl or aza-cycloduodec-1-yl radical which is, if required, substituted by alkyl groups or possesses one or more double bonds as said above. One, two or more alkyl groups may be present as substituents, and optionally two identical or different alkyl groups may be present on one and the same ring carbon atoms of the aza-cycloaliphatic ring.

Amongst the monocyclic aza-cycloaliphatic substituents in the 3-position of the rifamycin compounds mentioned, the following should primarily be pointed out: an azetidin-1-yl (trimethyleneimine) radical which is substituted in the β-position and optionally also in the α-position, by lower alkyl groups with 1–7 carbon atoms, the pyrrolidino radicals which are monosubstituted or polysubstituted in the β-positon and optionally also in the β'-position by lower alkyl groups with 1–7 carbon atoms, such as methyl, ethyl, propyl, isopropyl, butyl or sec. - or tert. - butyl groups, and the derivatives which are additionally substituted in the α-position or in the α,α'-positions by one of the alkyl groups mentioned, as well as the piperidino radicals mono- or polysubstituted in an analogous manner, in that is to say in β,γ,β'-position and optionally also in α- and/or α'-position, by the said lower alkyl groups and the analogous derivatives of hexahydro-1H-azepine or of octahydroazocine, which are mono- or polysubstituted in the β,γ,γ',β' or β,γ,δ,γ,',β'-positions respectively and optionally also in the αand/or α'-position by the said lower alkyl groups. As specific radicals there may for example be mentioned: the 3-methyl-azetidin-1-yl, the 3,3-dimethyl-azetidin-1-yl, the 3,3-diethyl-azetidin-1-yl, the 3,3-dipropyl-azetidin-1-yl, the 3-isopropyl-3-phenylazetidin-1-yl, the 3-methyl-pyrrolidino, the 3,3-dimethyl-pyrrolidin-1-yl, the 2,4,5-trimethylpiperidino, the 3,3 4,4-tetramethylpyrrolidin-1-yl, the 4-ethyl-piperidino, the 2,3-dimethyl-piperidino, the 2,4-dimethyl-piperidino, the 2,5-dimethyl-piperidino, the 4-methyl-3-ethyl-piperidino, the 2,3,4-trimethyl-piperidino, the 3-benzyl-piperidino, the benzyl-piperidino, the 2-methyl-4-phenyl-piperidino, the 2-methyl-5-phenyl-piperidino, the 4-(2'-phenylethyl)-piperidino, the 3-methyl- or 4-methyl-piperidino, the 4-isopropyl-piperidino, the 3,3-dimethyl-piperidino, the 3,4-dimethyl-piperidino, the 3,5-dimethyl-piperidino, the 4,4-dimethyl-piperidino or the 4-ethyl-piperidino radical, and also the 3- or 4-methyl- or -ethyl-hexahydroazepin-1-yl, the 3,3-dimethyl- or 4,4-dimethyl-hexahydroazepin-1-yl, the 2,3,4,trimethyl or triethyl-hexahydroazepin-1-yl, the 3- or 4-methyl- or ethyl-octahydro-azocin-1-yl, the 3,3-dimethyl- or 4,4-diethyl- or 5,5-dimethyl- or diethyl-cotahydroazocin-1-yl radical.

As further preferred possible substituents in the 3-position of the rifamycin compounds mentioned there should be mentioned the radicals of the unsaturated derivatives of the unsubstituted aza-cycloaliphatic rings or of the aza-cycloaliphatic rings substituted by the above-mentioned hydrocarbon radicals, especially those with 4–11 ring carbon atoms, that is to say for example of pyrrolidine, piperidine, hexahydroazepine, octahydroazocine, octahydroazonine, decahydroazecine, aza-cycloundecan and aza-cycloduodecane.

The following may be mentioned particularly: the $\Delta^3$- pyrrolino and $\Delta^3$-piperidino (1,2,3,6-tetrahydropyridyl-1) radical and their derivatives which are for example substituted by lower alkyl groups with 1 to 7 carbon atoms or phenyl radical as described above for the saturated compounds, for example the 4-methyl-$\Delta^3$-piperidino, the 3,4-dimethyl-$\Delta^3$-piperidino, the 4-ethyl-$\Delta^3$-piperidino, the 3-methyl-$\Delta^3$-piperidino, the 3,5-dimethyl-$\Delta^3$-piperidino, the 4-propyl-$\Delta^3$-piperidino or the 4-isobutyl-$\Delta^3$-piperidino radical and the 4-phenyl-$\Delta^3$-piperidino radical.

Bicyclic aza-cycloaliphatic substituents in the 3-position of the rifamycin compounds mentioned, primarily those with 4–11 carbon atoms in the heterocyclic ring, are for example those which possess one or more fused aromatic nuclei. These nuclei can in turn be monocyclic or polycyclic and can optionally be substituted by further aliphatic, cycloaliphatic, araliphatic or aromatic hydrocarbon radicals, especially by lower alkyl radicals with 1 to 7 carbon atoms. Benzene and naphthalene nuclei should be particularly highlighted. Specific examples of azabicyclic or polycyclic cycloaliphatic hydrocarbon radicals of this type are: the isoindolin-2-yl, the benz[f]isoindolin-2-yl, the benz[e]isoindolin-2-yl, the 1,2,3,4,-tetrahydro-isoquinol-2-yl, the 2,3,4,5-tetrahydro-1H-2-benzazepin-2-yl, the 2,3,4,5-tetrahydro1H-3-benzazepin-3-yl, the 1,2,3,4,5,6-hexahydro-2-benzazocin-2-yl, the 1,2,3,4-tetrahydrobenz[h]isoquinol-2yl or the 2,3-dihydro-1H-benz[de]isoquinol-2-yl, the 6,7-dihydro-5H-dibenz[c,e]azepin-6-yl, or the 5,6,7,8-tetrahydro-dibenz[c,e]azocin-6-yl radical.

Cycloaliphatic rings which are fused to the azacycloaliphatic ring in the 3-position of the rifamycin constituent are those of cycloalkanes or cycloalkenes with preferably 3–8 carbon atoms, such as for example cyclopropane, cyclobutane, cyclopentane or cyclohexane rings which can in turn be substituted, especially by lower alkyl radicals having 1 to 7 carbon atoms such as methyl groups. Such condensed ring systems are bicyclic or polycyclic aza-cycloaliphatic hydrocarbon radicals such as azabicyclo- or azatricyclo-alkyls or -alkenyls, optionally substituted by lower alkyl group having 1 to 7 carbon atoms, especially methyl groups. These, however, also result from bridging two carbon atoms at a time of the aza-cycloaliphatic ring, for example of the above-mentioned pyrrolidine, piperidine, hydroazepine or hydroazocine rings, by means of a single carbon to carbon bond or by means of straight or branched lower aliphatic alkylene radicals with 1 to 7 carbon atoms, such as the methylene or the ethylene, propylene, butylene or pentylene radicals or by means of alkylidene radicals such as the isopropylidene radical. Such radicals are for example the octahydroindol-1-yl, octahydroisoindol-2-yl, decahydrocyclohepta[b]pyrrol-1-yl, the decahydro-cyclohepta[c]-pyrrol-2-yl, the decahydro-5H-cyclohepta[b]-pyrid-1-yl, the decahydro-1H-cyclohepta[c]-pyrid-2-yl, the decahydro-cyclopent[c]-azepin-2-yl, the decahydro-cyclopenta[d]-azepin-3-yl, the 10-azabicyclo[4.3.1]-dec-10-yl, the 8-azabicyclo[4.3.1]-dec-8-yl, the decahydroquinol-1-yl and -isoquinol-2-yl, the 2-azabicyclo-[2.2.0]-hexy-2-yl, the 2-azabicyclo-[3.2.0]-hept-2-yl, the 7-azabicyclo-[4.2.0]-oct-7-yl, the 2-azabicyclo-[4.3.1]-dec-2-yl, the 9-azabicyclo-[3.3.2]-dec-9-yl, the 11-azabicyclo-[4.4.1]-undec-11-yl, the 3-azabicyclo-[4.1.0]-hept-3-yl, the 3-azabicyclo-[3.2.0]-hept-3-yl, the 3-azabicyclo-[3.1.1]-hept-3-yl, the 7-azabicyclo-[2.2.1]-hept-7-yl, the 2-azabicyclo[2.2.1]-hept-2-yl, the 7-azabicyclo-[2.2.1]-hept-7-yl, the 3-azabicyclo[3.1.0]-hex-3-yl, the 3-azabicyclo [3.3.0]-oct-3-yl, the 9-azabicyclo-[4.2.1]-non-9-yl, the 9-azabicyclo-[3.3.1]-non-9-yl, the 2-azabicyclo[3.3.1]-non-2-yl, the 3-azabicyclo[3.3.1]-non-3-yl, the 2-azabicyclo[3.2.2]-non-2-yl, the 9-azabicyclo-[3.3.1]-non-2-en-9-yl, the 2-azabicyclo[3.2.2]-nona-5,7,8-trien-2-yl, the 2-azabicyclo-[3.2.2]-nona-3,5,7,8-tetraen-2-yl, the 2-azabicyclo[4.2.0]-oct-2-yl, the 3-azabicyclo-[4.1.1]-oct-3-yl, the 8-azabicyclo[3.2.1]-oct-8-yl, the 8-azabicyclo[3.2.1]-oct-2-en-8-yl, the 6-azabicyclo-[3.2.1]-oct-6-yl, the 4-azabicyclo[5.4.0]-undec-4-yl, the 7-azabicyclo[4.3.0]-non-3-en-7-yl, the 8-azabicyclo[4.3.0]-non-3-en-8-yl, the 8-azabicyclo[4.3.0]-non-1(6)-en-8yl, the 1,8,8-trimethyl-3-azabicyclo-[3.2.1]-oct-3-yl, the 9-azabicyclo-[4.2.1]-nona-2,4-dien-9yl, the 3-azabicyclo-[4.4.0]-dec-1(6)-en-3-yl, the 2-azabicyclo[3.2.1]-oct-2-yl, the 3-azabicyclo[3.2.1]-oct-3-yl, the 2-azabicyclo-[2.2.2]-oct-2-yl, the 2-azabicyclo[2.2.2]-octa-4,6,7-trien-2-yl, the 2-azabicyclo[4.3.0]-non-2-yl, the 7-azatricyclo[3.3.0.0$^{1,3}$]-oct-7-yl, the 3-azatricyclo-[3.2.1.0$^{2,4}$]-oct-3-yl, the 4,7-methano-3a,4,7,7a-tetrahydro-isoindolin-2-yl, the 4,7-methano-3a,4,5,6,7,7a-hexahydro-isoindolin-2-yl, the 1,5-methanocyclopent[c]1,2,3,4,5,5a,6,8a-octahydroazepin-2-yl, the 1,5-methano-cyclopent[d]decahydro-azepin-3-yl and the 1H-methano-3,4,5,6-tetrahydro-3-benzazocin-3-yl radical.

Finally, spirocyclic aza-hydrocarbons radicals should also be mentioned, such as for example the 2-azaspiro-[3.3]-hept-2-yl, 1-azaspiro[4.5]-dec-1-yl, the 2-azaspiro[4.5]dec-2-yl, the 8-azaspiro[4,5]dec-8-yl, the 5-azaspiro[2.4]hept-5-yl, the 5-azaspiro[2.4]hept-4-en-5-yl, the 2-azaspiro[4.4]non-2-yl, the 2-azaspiro[4.6]undec-2-yl, the 1-azaspiro[5.5]undec-1-yl, the 3-azaspiro [5.5]dec-3-yl, the 3-azaspiro[5.5undec-3-yl, the 6-azaspiro[2.5]oct-6-yl, the 2-azaspiro[3.4]oct-2-yl, the 6-azaspiro[3.4]oct-6-yl, the 2-azaspiro[3.5]non-2-yl, the 7-azaspiro[3.5]non-7-yl, the 3-azaspiro[5.6]dodec-3-yl, the 6-azaspiro[4.4]-oct-6-yl, the 3-azaspiro[5.5]undec-7-en-3-yl radical and those which also contain an aromatic nucleus such as the spiro[cyclohexane-1,1'(2'H)-isoquinol -2'-yl], the spiro[naphthalene-1(4H), 3'-piperid-1'-yl], the spiro[-naphthalene-1(2H), 4'-piperid-1'-yl], the spiro[cyclohexane-1,4'(1'H)-quinol-1'-yl], the spiro[cyclohexane-1,4'(3'H)isoquinol-2'-yl]or the spiro[naphthalene-2(1H), 4'-piperid-1'-yl] radical, and the derivatives thereof substituted in any positions by lower alkyl groups having from 1 to 7 carbon atoms, especially methyl groups.

As outstanding examples of the new selected group of 3-amino rifamycin derivatives, as defined above, and which are active also against rifampicin resistant microorganisms, the following may be pointed out:

3-(3'-methyl-piperidino)-rifamycin SV, 3-(4'-methyl-piperidino]-rifamycin SV, 3-(3',4'-dimethyl-piperidino)-rifamycin SV, 3-(3',5'-dimethyl-piperidino)-rifamycin SV, 3-(4',4'-dimethylpiperidino)-rifamycin SV, 3-(3'-methyl-pyrrolidino)-rifamycin SV, 3-(4'-ethyl-piperidino)-rifamycin SV, 3-(4'-isopropylpiperidino)-rifamycin SV, 3-(3',3'-dimethyl-pyrrolidino)-rifamycin SV, 3-(3'-methyl-3'-ethyl-piperidino)-rifamycin SV, 3(4'-tert.butyl-piperidino)-rifamycin SV, 3-(3',3'-dimethyl-piperidino)-rifamycin SV, 3-(4'-phenyl-piperidino)-rifamycin SV, 3-(3'-phenyl-pyrrolidino)-rifamycin SV, 3-(4'-cyclohexyl-piperidino)-rifamycin SV, 3-(3'-cyclohexyl-pyrrolidino)-rifamycin SV, 3-(4'-benzyl-piperidino)-rifamycin SV, 3-(isoindolin-2-yl)-rifamycin SV, 3-(octahydroisoindol-2-yl)-rifamycin SV, 3-(1',2',3',4'-tetrahydroisoquinol-2'-yl)-rifamycin SV, 3-(4'-cyclohexylpropyl-piperidino)-rifamycin SV, 3-(4'-cyclohexylmethyl-piperidino)-rifamycin SV, 3-(4'-tert.butyl-hexahydroazepino)-rifamycin SV, 3-(3'-azabicyclo[3'2'1']-oct-3'-yl)-rifamycin SV, 3-(1',8',8'-trimethyl-3'-aza-bicyclo[3',2',1']-oct-3'-yl)-rifamycin SV and the corresponding rifamycin S derivatives.

The above-mentioned 3-(3'-methyl-piperidino)-rifamycin SV, 3-(4'-methyl-piperidino)-rifamycin SV, 3-(4',4'-dimethyl-piperidino)-rifamycin SV, 3-(4'-ethyl-piperidino)-rifamycin SV, 3-(3',4'-dimethyl-piperidino)-rifamycin SV, 3-(3',5'-dimethyl-piperidino)-rifamycin SV and 3-(4'-isopropyl-piperidino)-rifamycin SV, in the dilution test inhibit rifampicin-resistant clones of Staphylococcus aureus SG 511 which have been selected by addition of rifampicin in the above-mentioned concentration to sensitive populations of this microorganism in the above-mentioned concentration, at a concentration (minimum inhibitory concentration) of about 1-8 mcg/ml.

The 3-amino-rifamycin S and SV derivatives and their derivatives hydrogenated in at least one of the positions 16, 17; 18, 19; 28, 29 according to the present invention are also useful as additives to animal fodders and as disinfectants, for example for preserving victuals.

Another special class of 3- amino rifamycin compounds coming into the purview of the present invention is formed by the following two groups of compounds
1. (compounds I) having the above formula (A)
2. (compounds II) represented by the hydroquinone form of compounds I)

wherein in the said formula Am denotes a 4R - 1-piperazinyl radical which is optionally substituted at the C atoms by lower alkyl groups, and wherein R represents a hydrocarbon radical of the following formula

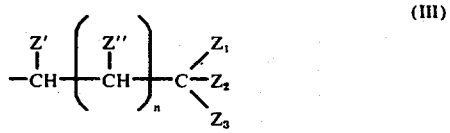

(III)

in which $n = 0$ or 1, $Z_1$ represents a lower alkyl or lower alkenyl group which can also be substituted by an unsubstituted or lower alkyl-substituted phenyl, cycloalkyl or cycloalkenyl group, or represents a phenyl group or an unsubstituted or lower alkyl-substituted cycloalkyl or cycloalkenyl group, it also being possible for the phenyl groups to be substituted by halogens, $Z_2$ denotes hydrogen or a lower alkyl or lower alkenyl group and $Z_3$ denotes a lower alkyl or lower alkenyl group or optionally together with $Z''$ denotes a double bond, and $Z_2$ and $Z_3$ together represent a lower alkylidene or lower alkenylidene group and $Z_1$ and $Z_3$ together represent an alkylene or alkenylene group, but $Z_1 + Z_2$ can also denote such an alkylene or alkenylene group if $Z_3$ together with $Z''$ represents a double bond, and $Z'$ and $Z''$ each represent hydrogen or a lower alkyl group, and in the cycloaliphatic groups mentioned, or in the cycloaliphatic groups formed by an alkylene or alkenylene group $Z_1 + Z_3$ or $Z_1 + Z_2$, one or more non-adjacent C—C atom pairs of the ring can optionally be bonded to one another directly, or indirecty via a lower alkylidene or alkylene group, or a C atom of a lower alkylene group can be spirocyclically substituted, and these groups do not possess more than 12 C atoms, and their salts and quaternary ammonium salts.

With reference to these compounds (I) and (II) the terms in the above definitions are as follows:

By alkenyl or cycloalkenyl, or alkenylidene or alkenylene groups, there are to be understood hydrocarbon radicals with one or more double bonds.

Lower alkyl, lower alkenyl and lower alkylidene or lower alkenylidene groups are those with up to 7 C atoms, especially with 1-4 C atoms, such as, for example, methyl, ethyl, propyl, isopropyl, straight or branched butyl, pentyl, hexyl or heptyl groups bonded in any desired position, vinyl, allyl or methallyl, 1-propenyl, methylene, ethylidene, propylidene, butylidene, isopropylidene or isobutylidene groups. An alkylene or alkenylene group $Z_1 + Z_3$ together with the C atom of the abovementioned formula, to which it is bonded, forms a cycloalkyl or cycloalkenyl group with a total of not more than 12 C atoms, and here again a cycloalkenyl group is to be understood as a group with one or more double bonds. Preferably, straight or branched alkylene groups can be used which accordingly form cycloalkyl radicals with 3-8 ring C atoms and above all 5-6 ring C atoms or cycloalkenyl radicals with, preferably, 5-8 ring C atoms. Straight-chain alkylene groups or alkenylene groups together with the abovementioned C atom of the above formula give unsubstituted cycloaliphatic rings and in the case of branched alkylene groups the rings formed are substituted by alkyl groups, especially lower alkyl groups with 1-4 C atoms, above all methyl groups. Such cycloalkyl groups with 3-8 C atoms in the ring are, for example, cyclopropyl, cyclobutyl, cyclopentyl, cyclohexyl, cycloheptyl, 4-methylcyclohexyl, 2,6-dimethylcyclohexyl or 3,5-dimethylcyclohexyl groups or 1-methyl-4-isopropylcyclo hexyl (p-methyl) or 1-methyl-3-isopropylcyclohexyl (m-menthyl) groups.

Examples of cycloalkenyl groups which should be mentioned are: 1-cyclopenten-1-yl, 2-cyclopenten-1-yl, 3-cyclopenten-1-yl, 2,4-cyclopentadien-1-yl, 1-cyclohexen-1-yl, 2-cyclohexen-1-yl, 3-cyclohexen-1-yl, 1,3-cyclohexadien-1-yl and 1,4-cyclohexadien-1-yl, 1-p-menthen-4-yl, 2-p-menthen-1-yl, 3-p-menthen-1-yl or optionally other isomers of this group, or corresponding compounds with two double bonds, such as the hydrocarbon radicals of the terpinenes, of the phellandrenes, of the limonenes or of the menthadienes.

A cycloalkyl or cycloalkenyl group which may represent the radical $Z_1$ or occur in this radical or represent $Z_1 + Z_2$ together can also be unsubstituted or substituted by lower alkyl groups and has not more than 12 C atoms and is, above all, a cycloalkyl radical with 3-8 ring C atoms and especially 5-6 ring C atoms or a cycloalkenyl radical with 5-8 ring C atoms, these radicals being unsubstituted or substituted by lower alkyl groups, especially with 1–4 C atoms, above all methyl groups, and can be, for example, one of the specific groups of this type which have just been mentioned.

The cycloalkyl or cycloalkenyl groups can also be bridged directly or via a lower alkylidene or alkylene group, preferably with 1–4 C atoms, such as a methylene, ethylene or isopropylidene group, or can be spirocyclically substituted, that is to say they can also form polycyclic, especially bicyclic, systems, which are derived from polycycloalkanes or bicycloalkanes or spirocycloalkanes and their unsaturated derivatives. Such groups are, for example, the hydrocarbon radicals of bicyclohexanes, bicycloheptanes or bicyclooctanes and their derivatives substituted by lower alkyl groups, such as the hydrocarbon radicals of the bicyclic terpenes of the thujane, pinane or bornane group.

The abovementioned phenyl radicals can be unsubstituted or substituted by halogen, such as, for example, by chlorine, fluorine or bromine, or by lower alkyl radicals, that is to say those with 1–7 C atoms, especially by methyl groups.

The group R has preferably not more than 35 C atoms and in particular has between 4 and 16 C atoms.

Lower alkyl groups $Z'$ and $Z''$ in the indicated formula (III) are those with 1–7 C atoms, especially 1–4 C atoms, such as one of those mentioned above, but above all methyl groups.

Amongst the compounds (I) and (II) there are especially to be singled out those in which the group A denotes a 4R-1-piperazinyl radical which is unsubstituted at the C atoms and wherein R has one of the following formulae:

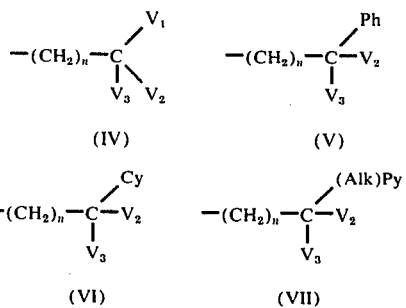

(IV)   (V)

(VI)   (VII)

wherein $n = 1$ or 2 and $V_1$ and $V_2$ each denote an alkyl or alkenyl group with 1–7 C atoms, $V_3$ denotes hydrogen or together with $V_2$ denotes an alkylidene or alkenylidene group with 1–7 C atoms, Ph denotes a phenyl group which is unsubstituted or substituted by chlorine or bromine atoms and/or methyl groups, Cy denotes a cycloalkyl or cycloalkenyl group with 5–8 ring C atoms, wherein the ring can optionally be substituted by lower alkyl groups with 1–4 C atoms, Py denotes a cycloalkyl or cycloalkenyl group of this type or a phenyl group as defined above and "Alk" denotes a straight-chain or branched alkylene group with 2–4 C atoms or an alkylidene group with 1–4 C atoms, and their derivatives which are substituted by a methyl group at one or both of the C atoms of the —(CH$_2$)$_n$ group. The said alkyl, alkenyl, alkylidene or alkenylidene groups with 1–7 C atoms are, for example, those mentioned above, in particular have 1–4 atoms and are, in particular, methyl, ethyl or propyl groups, or vinyl or allyl or methallyl groups or methylene, ethylidene, propylidene or isopropylidene groups or vinylidene or 2-propen-1-ylidene groups. The said alkylene group with 2–4 C atoms is in particular an ethylene or trimethylene group. A cycloalkyl or cycloalkenyl group Cy is, in particular, a group of this type with 5–6 ring C atoms, that is to say a cyclopentyl or cyclohexyl group, or a corresponding mono-unsaturated and/or lower alkyl-substituted hydrocarbon radical, such as, for example, one of those mentioned above. Preferably, 1–3 of the substituents mentioned are optionally present in the said phenyl groups or cycloalkyl rings. Such groups can also be bridged as described above and are then, say, radicals of the abovementioned type, for example radicals of the bicyclic terpenes which have been mentioned.

Derivatives of the compounds just mentioned having the partial formulae (IV) – (VI), wherein $V_3$ denotes an alkyl or alkenyl group with 1–7, for example 1–4, C atoms, are also of interest.

A class of compounds (I) and (II) which is also preferred are compounds in which the group A denotes a 4R-1-piperazinyl radical which is unsubstituted at the C atoms and wherein R has the following formula:

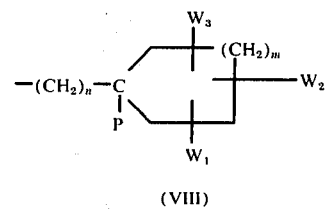

(VIII)

wherein $n = 1$ or 2 and $m = 1$–4, P = H or lower alkyl with 1–4 C atoms, and $W_1$, $W_2$ and $W_3$ denote lower alkyl and/or alkenyl groups with 1–4 C atoms which are optionally present at any desired ring C atom, their derivatives which are unsaturated in the cycloaliphatic ring of the formula VIII, and derivatives of these compounds with a bridged cycloaliphatic ring according to formula VIII, especially those in which two non-adjacent C atoms are endocyclically bonded to one another by a direct C,C bond or via a lower alkylidene or alkenylene group with 1 or 2–4 C atoms, and/or derivatives of these compounds which are substituted at one or both of the C atoms of the group (CH$_2$)$_n$ by a methyl group. Examples of saturated and unsaturated cycloaliphatic rings according to the formula VIII are to be found amongst those generally mentioned above for the compounds (I) and (II), from which it can be seen that in the case of the unsaturated rings it is above all 1- or 2-double bonds which are concerned. The lower alkyl or alkenyl groups which are particularly concerned, and the bridging groups in the bicyclic or polycyclic radicals are, in particular, those mentioned above for the similar cycloaliphatic groups Cy. In particular, in these compounds, $m = 1$ or 2. Such rings, if they are substituted, particularly carry 1–2 methyl groups.

Amongst the compounds of the present invention having the partial formulae (III) – (VIII) for the radical R according to the above definition, compounds of particular importance are those wherein $n = 1$, and in turn particularly those in which the radicals $V_1$–$V_3$, Py, Cy and Alk in the formula (VII) have the meaning specified above or in the formula VIII P = H and the cycloaliphatic ring is a cyclopentyl or cyclohexyl ring or a corresponding radical which is mono-unsaturated and/or substituted by methyl groups, especially 1–2 methyl groups.

The new compounds (I) and (II) include, for example, 3-(4-isobutyl-1-piperazinyl)-rifamycin S and SV, 3-[4-(2-ethylbutyl)-1-piperazinyl]-rifamycin S and SV, 3-[4-(2-methylbutyl)-1-piperazinyl]-rifamycin S and SV, 3-[4-(2-methylpentyl)-1-piperazinyl]-rifamycin S and SV, 3-[4-(2-phenylpropyl)-1-piperazinyl]-rifamycin S and SV, 3-(4-methallyl-1-piperazinyl)-rifamycin S and SV, 3-[4-(2-methyl-3-butenyl)-1-piperazinyl]-rifamycin S and SV, 3-(4-cyclohexylmethyl-1-piperazinyl)-rifamycin S and SV, 3-[4-(4-methylcyclohexylmethyl)-1-piperazinyl]-rifamycin S and SV, 3-[4-(4-tert. butylcyclohexylmethyl)-1-piperazinyl]-rifamycin S and SV, 3-[4-(4-isobutylcyclohexylmethyl)-1-piperazinyl]-rifamycin S and SV, 3-[4-(4-isopropylcyclohexylmethyl)-1-piperazinyl]-rifamycin S and SV, 3-[4-(3-methylcyclohexylmethyl)-1-piperazinyl]-rifamycin S and SV, 3-[4-(3,4-dimethylcyclohexylmethyl)-1-piperazinyl]-rifamycin S and SV, 3-[4-(3,5-dimethylcyclohexylmethyl)-1-piperazinyl]-rifamycin S and SV, 3-[4-(3-cyclohexenylmethyl)-1-piperazinyl]-rifamycin S and SV, 3-(4-cyclopropylmethyl-1-piperazinyl)-rifamycin S and SV, 3-(4-cycloheptylmethyl-1-piperazinyl)-rifamycin S and SV, 3-[4-(2-cyclohexylpropyl)-1-piperazinyl]-rifamycin S and SV or 3-[4-(2-cyclohexylbutyl-1-piperazinyl]-rifamycin S and SV, 3-(4-cyclooctylmethyl-1-piperazinyl)-rifamycin S and SV, 3-[4-(2-methylcyclohexylmethyl)-1-piperazinyl]-rifamycin S and SV and 3-[(bicyclo[2.2.1]hept-2-yl-methyl)-1-piperazinyl]-rifamycin S or SV.

The compounds (I) and (II) are distinguished, relative to the other compounds of the present invention and also relative to other known rifamycin derivatives having an antituberculosis action, by having a greater anti-tuberculosis action, as can be demonstrated in animal experiments, for example on mice. Thus the compounds, when administered perorally to mice infected with *Mycobacterium bovis*, show a pronounced tuberculostatic action in doses of between 1 mg/kg and 40 mg/kg. For example, 3-(4-isobutyl-1-piperazinyl)-rifamycin SV in this test shows an $ED_{50}$ of 1 mg/kg. 3-(4-Cyclohexylmethyl-1-piperazinyl)-rifamycin SV in the same test also shows an $ED_{50}$ of 1 mg/kg. In addition, the compounds are distinguished by very great therapeutic breadth in that a significant toxicity only manifests itself at a very high dose. Thus, for example, the oral $LD_{50}$ in the case of the last-mentioned specific compounds is greater than 5,000 mg/kg.

The high anti-tuberculosis action can also be demonstrated by in vitro experiments. Thus the minimum inhibitory concentration in vitro against *Mycobacterium bovis* is 30 times lower in the case of the above-mentioned 3-(4-isobutyl-1-piperazinyl)-rifamycin SV than in the case of the known tuberculostatic rifamycin medicament Rifampicin, namely 3-(4-methyl-1-piperazinyl-iminomethyl)-rifamycin SV.

The compounds also have a good anti-bacterial action, as can also be demonstrated in animal experiments, for example on mice. Thus they show a pronounced antibacterial action on mice infected with staphylococci, when administered perorally in doses of between 0.2 and 40 mg/kg.

The new compounds can therefore be used as medicaments, above all for tubercular infections, but also for other infections such as, for example, leprosy, or infections caused by pyogenic germs, such as, for example, staphylococci. The new compounds are, however, also valuable intermediate products for the manufacture of other useful materials, especially of pharmacologically active compounds.

The 3-amino-rifamycin S or SV compounds of their derivatives of the present invention may be obtained by a process, wherein rifamycin S or one of the mentioned hydrogenated derivatives of rifamycin S partially hydrogenated in one of the positions 16, 17; 18, 19; 28, 29 is reacted with ammonia or with an amine AmH corresponding to the amino group Am as defined in the above formula (A), and the 3-amino rifamycin S or SV compound formed or one of their products hydrogenated in the aliphatic side chain is isolated from the reaction mixture and/or, if desired, a hydroquinone obtained before or after the isolation is oxidised to form the corresponding quinone or a quinone is reduced to form the corresponding hydroquinone, and/or if, desired, any rifamycin S or SV compound so obtained is catalytically hydrogenated to form a derivative of rifamycin SV partially hydrogenated in at least one of the positions 16, 17; 18, 19; 28 and 29.

The reaction of rifamycin S or one of the said hydrogenated derivatives with the amine is advantageously carried out in a solvent that is free from hydroxyl groups, for example in chloroform, methyl cellosolve, tetrahydrofuran or especially in a non-polar solvent, for example in an aromatic hydrocarbon such as benzene, or preferably in dioxan. When dioxan is used, the reaction is as a rule complete within about 5 to 10 minutes. It has been observed that the reaction speed depends also on the structure of the amine. It is advantageous to use a large excess (5 to 10 mols) of amine. When the amine is liquid the addition reaction to the rifamycin compound can also be effected in the absence of a solvent, the amine itself being used as such. The reaction is advantageously performed at room temperature or — when it progresses slowly — at an elevated temperature. The progress of the reaction can be checked by thin-layer chromatography. In general, the reaction solution contains the reaction product partially in the form of the quinone and partially in the form of the hydroquinone. It is advantageous to oxidize the product of the reaction solution completely to the quinone and to isolate the latter. The oxidation is advantageously carried out with an inorganic oxidant, for example hydrogen or ammonium persulphate, or preferably with potassium ferricyanide. The quinone or hydroquinone can be extracted with organic solvents.

The conversion of quinones and hydroquinones into one another which is optionally to be carried out after the isolation can be carried out accordingly to the methods discussed above.

The hydrogenation of the aliphatic side chain in the rifamycin component, which is to be carried out in accordance with the invention, can advantageously be carried out with catalytically activated hydrogen, for example using palladium or platinum catalysts, or by means of Raney nickel.

The preferred use is made of amines that yield the above-mentioned, particularly potent final products.

In the case of the above compounds (I) and (II) another process can also be used for preparation, in that the unsubstituted piperazinyl radical or the piperazinyl radical substituted at the C atoms is first introduced in the above mentioned manner into the 3-position of rifamycin S or rifamycin SV, and the radical R is then introduced into the N' position of the piperazinyl radical by reaction with an alkylating agent.

In this reaction of 3-(1-piperazinyl)-rifamycin S or SV or of its abovementioned C-methyl homologues with the alkylating agent mentioned, alkylating agents of the formula XR are used in particular, wherein X denotes a halogen, such as, for example, chlorine, bromine or iodine, or the radical of an oxygen-containing inorganic acid, such as a sulphuric acid or sulphurous acid, or of a halogenosulphuric acid, such as, in particular, fluorosulphonic acid. Such alkylating agents are thus, for example, alkyl halides, such as, for example, the bromides, iodides or chlorides of the hydrocarbon radical R, or the R-monoesters or R-diesters of sulphuric acid or of fluorosulphonic acid.

The reaction of the said rifamycin compound with these alkylating agents is preferably carried out in the presence of a base, especially of a strongly basic, non-nucleophilic tertiary amine, in particular an amine of the formula

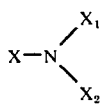

wherein X denotes a lower alkyl group and $X_1$ and $X_2$ each denote a bulky aliphatic hydrocarbon radical. The groups $X_1$ and $X_2$ are, for example, lower alkyl groups with 1–12 C atoms, preferably with 1–7 C atoms, which have a branched carbon chain, whilst X preferably denotes a lower alkyl group with 1–7 C atoms. Above all, the so-called Hünig's base, that is to say ethyl-diisopropylamine, is used.

The reaction is advantageously carried out in an inert solvent, such as, in particular, a chlorinated aliphatic hydrocarbon, for example methylene chloride, or an alcohol, such as methanol, at temperatures between room temperature and approx. 100°, using 1 mol each of the rifamycin compound and of the alkylating agent and also preferably adding the base in an equimolar ratio. The reaction time varies according to the reactants and can be from half an hour to 24 or 48 hours.

The new compounds may be used, for example, in the form of pharmaceutical preparations containing them in conjunction or admixture with an organic or inorganic, solid or liquid pharmaceutical excipient suitable for enteral, local or parenteral administration. Suitable excipients are substances that do not react with the new compounds, for example water, gelatin, lactose, starches, stearylalcohol, magnesium stearate, talcum, vegetable oils, benzyl alcohols, gums, propyleneglycol, polyalkyleneglycols, white petroleum jelly, cholesterol or other known medicinal excipients. The pharmaceutical preparations may be, for example, tablets, capsules, dragees, ointments, creams or capsules, or in liquid form solutions, suspensions or emulsions. They may be sterilized e.g. by leaf or by filtration and lyophilisation and/or contain assistants such as preserving, stabilizing, wetting or emulsifying agents, solution promoters, salts for regulating the osmotic pressure or buffers. They may also contain other therapeutically valuable substances. The preparations are formulated by the usual methods.

The new compounds may also be used in veterinary medicine, for example in one of the forms mentioned above.

The following Examples illustrate the invention.

The hydroquinones of Examples 2–14 and 18–19 are prepared by reduction of the quinones as performed in Example 1.

The thin-layer chromatograms in any of the Examples 1–19 have been carried out on silica gel in the following systems A, B and C:

System A: Benzene+acetone (4:1), plate impregnated with citric acid (52 ml of 5% citric acid solution per 25 g of silica gel)

System B: Chloroform+methanol (9:1), plate not impregnated

System C: Benzene+acetone (2:1), plate impregnated with citric acid (52 ml of 5% citric acid solution per 25 g of silica gel).

The Rf values set forth in Examples 1–19 are referred to the Rf value of rifamycin S = 1 and are designated in the Examples as $R_s(A)$, $R_s(B)$ and $R_s(C)$.

EXAMPLE 1

A solution of 50g of rifamycin S in 200 ml of dioxane is mixed with 12g of methylamine and the batch is kept for 10 minutes. Then chloroform, water and an aqueous solution of 50g of potassium ferricyanide are added and the whole is vigorously agitated for some time, then neutralized, and the residue is chromatographed on silica gel, performing the elution with chloroform with a gradient of methanol. The resulting 3-methylamino-rifamycin S, which is quickly eluted in a reddish brown solution, displays an $R_s(A)$ value of 0.48; it is evaporated, crystallized from ether and then from methanol or aqueous alcohol; it has a melting point of 243° to 244° C (from aqueous methanol; dark red prisms).

The nuclear magnetic resonance spectrum of the compound does not contain the signal appearing in the case of rifamycin S for hydrogen on $C_3$. The mass spectrum of 16, 17, 18, 19, 28, 29-hexahydro-3-methylamino-rifamycin S (obtained by catalytic hydrogenation, for example on 10% palladium charcoal in ethanol under atmospheric pressure at room temperature) corresponds to this formula.

Reduction with ascorbic acid furnishes yellow 3-methylamino-rifamycin SV melting at 185° C.

5 Grams of 3-methylamino-rifamycin S are dissolved in as little methanol as necessary, excess ascorbic acid is added and a sufficiency of water just to leave the solution still clear. The initially dark red solution gradually turns yellow. When the solution has become pure yellow, much water is added and the batch is extracted with chloroform until the aqueous phase remains colourless. The combined chloroform extracts are washed with sodium chloride solution, dried and evaporated. The evaporation residue crystallizes from 90% aqueous methanol or methanol in yellow prisms. $R_{s(C)} = 0.62$.

EXAMPLE 2

When in the reaction described in Example 1 methylamine is replaced by 16g of ethylamine, 3-ethylamino-rifamycin S melting at 258° to 260° C is obtained (from methanol). $R_{s(A)} = 0.64$. The corresponding hydroquinone has an $R_{s(C)}$ value of 0.70.

EXAMPLE 3

When 50g of rifamycin S is reacted with 22g of ethanolamine as described in Example 1, 3-(2'-hydroxyethylamino)-rifamycin S melting above 340° C is obtained (from methanol+ether). $R_{s(A)} = 0.42$. The corresponding hydroquinone decomposes above 185° C. $R_{s(C)} = 0.46$.

EXAMPLE 4

A solution of 30g of rifamycin S in 200ml of dioxane is heated on a boiling waterbath, 12.5g of isopropylamine are added and heating is continued until the initially deep violet solution has turned yellowish brown. It is then rapidly cooled, then chloroform, water and an aqueous solution of 30g of potassium ferricyanide are added and the whole is vigorously agitated for some time. The batch is then neutralized, and the chloroform phase is isolated, dried and evaporated. The residue is chromatographed on silica gel, performing the elution with chloroform with a gradient of methanol. The 3-isopropylamino-rifamycin S, which displays in the thin-layer chromatogram an $R_{s(A)}$ value of 0.72, is contained in the brownish red, rapidly travelling portions of the eluate. The product is crystallized from aqueous methanol, to yield 5.5g of dark red crystals melting at 168° to 170° C.

The corresponding hydroquinone melts at 165° to 170° C (from aqueous methanol). $R_{s(C)} = 0.77$.

EXAMPLE 5

The reaction of 50g of rifamycin S with 36g, of n-hexylamine as described in Example 1 gives rise to 3-hexylamino-rifamycin S as an amorphous substance. $R_{s(A)} = 1.00$. The corresponding hydroquinone displays an $R_{s(C)}$ value of 0.86.

EXAMPLE 6

The reaction of 50g of rifamycin S with 36g of cyclohexylamine as described in Example 4 gives rise to 3-cyclohexylamino-rifamycin S as an amorphous substance. $R_{s(A)} = 1.00$.

The corresponding hydroquinone crystallizes from ether. It melts at 161° to 162° C. $R_{s(C)} = 0.85$.

EXAMPLE 7

50 Grams of rifamycin S are dissolved in 200ml of dioxane, 42g of N,N-diethyl-ethylenediamine are added and the whole is left to itself until the initially deep violet solution has turned yellowish brown. Then chloroform, water and an aqueous solution of 50g of potassium ferricyanide are added, and the whole is vigorously agitated for some time, then neutralized, and the chloroform phase is separated. The resulting 3-(2'-diethylamino-ethylamino)-rifamycin S is repeatedly extracted from the chloroform solution by means of citric acid solution of 1% strength. The citric acid solution is neutralized, agitated with chloroform, and the chloroform extract is dried and evaporated under vacuum. Chromatography of the evaporation residue on silica gel with chloroform and a gradient of methanol yields at first red and then violet-brown eluates that contain the desired product in pure form. The batch is evaporated and crystallized from alcohol or aqueous methanol. It forms blackish brown crystals that do not melt up to 300° C. $R_{s(B)} = 0.80$.

The corresponding hydroquinone has the following Rf values: $R_{s(C)} = 0.03$, $R_{s(B)} = 0.44$.

EXAMPLE 8

A solution of 50g of rifamycin S in 200ml of dioxane is mixed with 50g of amino-acetaldehyde diethylacetal, and the mixture is left to itself until the initially deep violet solution has turned yellowish brown. Then chloroform, water and an aqueous solution of 50g of potassium ferricyanide are added, and the batch is vigorously agitated for some time, neutralized, and the chloroform phase is separated, dried and evaporated. The evaporation residue is dissolved in a mixture of equal parts of dioxane and 2N-hydrochloric acid and left to itself for 15 minutes, then diluted with sodium chloride solution, extracted by agitation with ether, and the ether phase is dried and evaporated. For purification the evaporation residue is repeatedly chromatographed on silica gel, using for the elution ether or chloroform with a methanol gradient. The violet-brown fractions contain 3-formylmethylamino-rifamycin S. $R_{s(A)} = 0.80$. $R_{s(C)}$ of the corresponding hydroquinone: 0.91.

EXAMPLE 9

30 Grams of rifamycin S are dissolved in 300ml of dioxane, 18g of piperidine are added, and the mixture is heated on a water bath until all rifamycin S had reacted (checked by thin-layer chromatography). Then chloroform, water and an aqueous solution of 30g of potassium ferricyanide are added, and the whole is vigorously agitated for some time, then neutralized, and the chloroform phase is separated, dried and evaporated. The residue is purified by chromatography on silica gel with chloroform and a methanol gradient. The fractions of violet brown colour, which contain 3-piperidino-rifamycin S of $R_{s(A)} = 1.10$, are collected. On crystallization from ether the substance is obtained in coarse, black crystals melting at 200° C.

The corresponding hydroquinone, obtained by crystallization from methanol, melts at 190°–191° C. $R_{s(C)} = 1.11$.

EXAMPLE 10

100 Grams of rifamycin S are dissolved in 800ml of dioxane, 70g of N-methylpiperazine are added, and the mixture is heated on a water bath until all rifamycin S has reacted (checked by thin-layer chromatography). Then chloroform, water and an aqueous solution of 100g of potassium ferricyanide are added, and the whole is vigorously shaken for some time, neutralized, and the chloroform phase is separated. The desired reaction product is extracted from the chloroform solution by repeated agitation with citric acid solution of 5% strength. The citric acid solution is neutralized, extracted with chloroform, and the extract is dried and evaporated under vacuum. The residue is filtered through 500g of silica gel, using as solvent chloroform containing 5 to 10% of methanol. The filtrate is evaporated and the residue crystallized from ether, to yield 3-(N'-methyl-piperazino)-rifamycin S in the form of red prisms melting at 169° C. $R_{s(B)} = 0.66$. When the compound is suspended in water and citric acid is added until all has dissolved, the citrate, melting at 197° to 200° C, is obtained, which crystallizes from water or aqueous methanol.

When 3-(N'-methylpiperazino)-rifamycin S is dissolved in methyl iodide, it gives rise to crystalline, dark reddish brown methoidide which decomposes above 200° C. When an aqueous solution of the methoidide is poured over a column of Amberlite IRA-400 (in the chloride form), the methochloride is obtained.

3-(N'-methylpiperazino)-rifamycin SV crystallizes from aqueous methanol and melts at 208° to 209° C. $R_{s(C)} = 0.00$, $R_{s(B)} = 0.28$.

EXAMPLE 11

50 Grams of rifamycin S are reacted with 35g of morpholine as described in Example 9. The resulting 3-morpholino-rifamycin S melts at 213° C (from methanol). $R_{s(A)} = 0.80$.

The corresponding hydroquinone crystallizes from aqueous methanol and melts at 243° to 244° C. $R_{s(C)} = 1.11$.

EXAMPLE 12

The reaction of 30g of rifamycin S with 31g of N-carbethoxy-piperazine as described in Example 9 yields 3-(N'-carbethoxy-piperazino)-rifamycin S which crystallizes from ether and does not melt up 340° C. $R_{s(A)} = 0.70$. $R_{s(C)}$ value of the corresponding hydroquinone: 1.11.

EXAMPLE 13

The reaction of 30g of rifamycin S with 16g of pyrrolidine as described in Example 9 gives rise to 3-pyrrolidino-rifamycin S melting at 189° C (from ether). $R_{s(A)} = 0.72$.

The corresponding hydroquinone has an $R_{s(C)}$ value of 0.91.

EXAMPLE 14

30 g of rifamycin S are dissolved in just the required quantity of dioxan, and the solution treated at room temperature, while stirring vigorously, with 30 g of N-(2-aminoethyl)-morpholine. After 6 minutes, the reaction is interrupted by the addition of chloroform and excess citric acid (cooling, stirring). The batch is diluted with water and extracted with chloroform. The chloroformic extract is agitated for quite some time with excess aqueous potassium ferricyanide solution which is maintained alkaline with sodium bicarbonate. The chloroformic solution is then dried and evaporated. For purification, the residue is chromatographed on 1.5 kg of silica gel using chloroform as running medium. Rifamycin S is eluated first which is followed by the desired reaction product viz 3-(2'-morpholino-ethyl)-Rifamycin S, in a dark wine-red solution. It is crystallized from ether, and recrystallized twice from aqueous methanol to obtain 4.8 g of coarse, dark red crystals which do not melt up to 350° C. $R_{s(B)} = 0.90$.

The corresponding hydroquinone has an $R_s(B)$ value of 0.36.

EXAMPLE 15

A solution of 20 g of rifamycin S in 30 ml of diethylamine is stirred for 30 minutes at room temperature. The reaction mixture is then evaporated, the residue dissolved in chloroform, and the chloroformic solution agitated for quite some time with an excess of aqueous potassium ferricyanide solution. After this, the chloroformic phase which meanwhile has assumed a brown-red colour is separated, dried with sodium sulfate, and evaporated. The residue is recrystallized once from ether and twice from methanol. There are obtained 5 g of red crystals of 3-diethylamino-rifamycin S of melting point 190°–191° C. $R_s(A) = 0.90$.

When a suspension of the red crystals of melting point 190°–191° C in aqueous methanol is treated with excess Na-ascorbate and stirred for some time, a clear yellow solution is obtained from which on acidification with aqueous citric acid solution the hydroquinone of the above substance, the -3-diethylamino-rifamycin SV crystallizes out. The crystals are filtered and washed with aqueous methanol containing some ascorbic acid. Yellow crystals of melting point 154° C. $R_s(A) = 0.82$.

EXAMPLE 16

20 ml of cyclopropylamine are added at room temperature to a solution of 20 g of rifamycin S in 20 ml of dioxan, and the mixture stirred and allowed to react for 3 minutes. The batch is then evaporated as rapidly as possible at 25° C, the residue dissolved in chloroform, and the solution reacted for a rather long time with an excess of an aqueous solution of potassium ferricyanide. The chloroform phase is then separated, washed with 3% citric acid solution, dried with $Na_2SO_4$, and evaporated. The residue is chromatographed on the 30- to 50-fold quantity of silica gel that has been washed with acid. The initially yellow-coloured eluate contains unchanged rifamycin S. The succeeding red portions contain the desired reaction product. The latter fractions are evaporated and the residue recrystallized from aqueous methanol to obtain red crystals melting at 162°–170° C constituting the 3-(cyclopropylamino)-rifamycin S. Yield, 3 g; $R_s(A) = 0.58$.

For reduction of the quinone of melting point 162°–170° C, the crystals are suspended in aqueous methanol and the suspension stirred while being treated with excess Na-ascorbate. After a short while a clear, yellow solution is obtained from which, after addition of citric acid and sodium chloride solution the desired hydroquinone can be extracted with chloroform. The hydroquinone 3-(cyclopropylamino)-rifamycin SV obtained on crystallization from aqueous methanol melts at 193°–195° C (decomposition); $R_s(A) = 1.0$.

EXAMPLE 17

30 g of rifamycin S are dissolved in as little dioxan as possible, and the solution treated at room temperature with 30 ml of benzylamine while stirring well. When but a slight quantity of rifamycin S can be detected by thin layer chromatography, the reaction is interrupted by the addition of ice, excess citric acid solution and chloroform. The chloroformic solution is vigorously stirred for some time with excess aqueous potassium ferricyanide solution, then isolated, dried and evaporated. The residue is chromatographed on 1.5 kg of silica gel using a 9:1 mixture of benzene and acetone as eluant. Rifamycin S is eluated first, and then the desired reaction product, 3-(benzylamino)-rifamycin S. For final purification, the latter is converted into the hydroquinone in the manner described in Example 16, and the hydroquinone recrystallized several times from ether. In this manner, 5g of 3-(benzylamino)-rifamycin SV of melting point 151°–152° C are obtained.

EXAMPLE 18

In a manner analogous to that of Example 9, 20 g of rifamycin S in 10 ml of dioxan are reacted with 20 ml of homopiperidine. The resulting 3-homopiperidino-rifamycin S, when recrystallized from ether, forms wine-red crystals melting at 218°–220° C (decomposition). The correpsonding hydroquinone crystallizes from methanol in the form of yellow prisms of melting point 190°–191° C. $R_s(A) = 1.30$.

EXAMPLE 19

In a manner analogous to that of Example 9, 30 g of rifamycin S in 20 ml of dioxan are reacted with 20 ml of N-methyl-tetrahydrofurfurylamine. Crystallization from ether yields more than 20 g of 3-(N-methyltetrahydrofurfurylamino)-rifamycin S in the form of black-violet crystals which melt at 211°–212° C. The corresponding hydroquinone has an $R_s(A)$ value of 1.10.

EXAMPLE 20

Pharmaceutical antibiotic preparation for parenteral use containing 3-morpholino-rifamycin SV as active ingredient: 50 mg of 3-morpholino-rifamycin SV-sodium salt are dissolved in 1 ml of distilled water. This solution is lyophylized at −30° C. The dry compound thus obtained is diluted with e.g. 50 ml of distilled water or 100 ml of physiological sodium chloride solution. These solutions are used for the parenteral administration of the antibiotic.

EXAMPLE 21

Pharmaceutical preparation containing 3-morpholino-rifamycin in the form of hard - gelatine capsules

| Composition | |
|---|---|
| 3-morpholino rifamycin SV | 150 mg |
| ethyl cellulose | 3 mg |
| stearic acid | 3 mg |
| | 156 mg |

MANUFACTURE

1. The ethyl cellulose and the stearic acid are dissolved in 20 times their weight of methylene chloride.
2. 3-Morpholino-rifamycin SV is mixed with solution (1) to form a homogeneous mass and this is passed through a sieve of 3–5 mm mesh at a temperature not exceeding 40° C.
3. The granulate (2) is passed through a sieve of 0.5 mm mesh and filled into hard gelatine capsules of size 1 (− 0.5 cm²).

In the same manner other similar pharmaceutical preparations can be obtained with any of the new 3-amino rifamycin S or SV derivatives of the present application, if desired, varying the doses in a suitable manner.

EXAMPLE 22

10 g (0.13 mol) of N-methylethanolamine are added to a solution of 21 g (0.03 mol) of rifamycin-S in 20 ml of dioxan and the whole heated for 15 minutes on a boiling water bath. The batch is then evaporated to dryness in vacuo and the residue chromatographed on 2kg of silica gel, using chloroform as eluant. In addition to a dark-colored head zone, two strong, yellow-colored bands are observed. The eluate of the more slowly eluted band is evaporated and the residue crystallized from aqueous methanol. After three crystallizations from aqueous methanol there is obtained 3-N-methylethanol-amino)-rifamycin-SV in the form of coarse prisms melting at 218° C (with decomposition.

Ultraviolet spectrum in 0.01-N alcoholic hydrochloric acid, m$\mu$ (log $\epsilon$): 244 (4.47), 262 (4.49), 333 (4.25), 408 (3.83).

NMR spectrum in CDCl$_3$: N-CH$_3$ signal at 2.79 (S, 3H).

EXAMPLE 23

20 g (0.22 mol) of N-ethylethanolamine are added to a solution of 25 g of (0.036 mol) of rifamycin-S in 25 ml of dioxan and allowed to stand at 20° C until the initially deep violet colored reaction mixture has turned a yellow-brown color. The reaction mixture is then evaporated to dryness in vacuo and the residue chromatographed on 2 kg of silica gel, using chloroform as eluant. In addition to a dark colored head zone, two strong, yellow-colored bands are observed. The eluate of the more slowly migrating band is evaporated and the residue crystallized from ethanol. After repeated crystallization from ethanol there is obtained 3-(N-ethylethanolamino)-rifamycin-SV in the form of coarse yellow crystals melting at 218° C (with decomposition).

Ultraviolet spectrum in 0.01-N alcoholic hydrochloric acid, m$\mu$ (log $\epsilon$): 245 (4.47), 263 (4.49), 334 (4.25), 407 (3.85).

EXAMPLE 24

6 g of rifamycin-S are gradually introduced in portions into 30 g of cycloheptylamine at 20° C while stirring thoroughly. As soon as the solution has turned a yellow-brown color, water is added, the mixture acidified with citric acid and extracted with chloroform. After drying and evaporating the chloroform extract, the residue is dissolved in methanol, reduced by the addition of aqueous ascorbic acid solution and again taken up with chloroform. The concentrated chloroform solution is chromatographed on 500 g of silica gel, using chloroform as eluant. In addition to a strong, dark head zone, two bands are observed. The eluate of the more rapidly migrating band is evaporated and crystallized twice from ether. 3(Cycloheptylamino)-rifamycin-SV is obtained in the form of yellow crystals which melt at 160° C with decomposition.

Ultraviolet spectrum in 0.01-N alcoholic hydrochloric acid, m$\mu$ (log $\epsilon$): 266 (4.59), 312 (4.22), 444 (4.09).

NMR spectrum in CDCl$_3$: methylene protons of the 7-ring produce a strong signal at 1.51 $\delta$

EXAMPLE 25

A mixture of 25 g of rifamycin-S, 50 ml of dioxan and 20 g of piperidine-4-carboxylic acid ethyl ester is allowed to stand for 12 hours at 20° C. Water is then added, the reaction mixture acidified with citric acid solution and extracted with chloroform. After evaporation of the chloroform extract, the residue is dissolved in methanol and treated with concentrated aqueous ascorbic acid solution. After standing for a short time, 3(4'-carboethoxypiperidino)-rifamycin-SV crystallizes out which, after recyrstallization from methanol, melts at 186°–187° C.

Ultraviolet spectrum in 0.01-N alcoholic hydrochloric acid m$\mu$ (log $\epsilon$): 223 (4.55), 295 (4.30),~320 (shoulder), 442 (3.93).

NMR spectrum in CDCl$_3$: OCH$_2$CH$_3$ at 1.23 $\delta$ ($t$, 3H) and OCH$_2$CH$_3$ at 4.11 ($q$, 2H).

EXAMPLE 26

25 g (0.25 mol) of 3-hydroxypiperidine are added to a solution of 25 g (0.036 mol) of rifamycin-S in 50 ml of dioxan and the whole allowed to stand for 12 hours at 20° C. The reaction mixture is then treated with water, acidified with citric acid and extracted with chloroform. The chloroform extract is stirred for 1 hour with an excess of aqueous potassium ferricyanide solution rendered alkaline with bicarbonate, then separated off, extracted with citric acid solution, dried and evaporated. The residue is dissolved in ether and 3-(3'-hydroxypiperidino)-rifamycin-S crystallizes out in the form of dark violet crystals. After two crystallizations from a mixture of methanol and water the product melts at 214° C (with decomposition).

Ultraviolet spectrum in ethanol, mµ (logε): 219 (4.50), 271 (4.47), 324 (4.21), 550 (3.45).

Infrared spectrum in $CH_2Cl_2$, $cm^{-1}$: 3460, 1735, 1710, 1670, 1620 etc. By reduction with ascorbic acid 3-(3'-hydroxypiperidino)-rifamycin-SV is formed which, after crystallization from a mixture of methanol and water, melts at 199°–200° C.

Ultraviolet spectrum in 0.01-N alcoholic hydrochloric acid, mµ (logε): 224 (4.57 ), 295 (4.28),~320 (shoulder), 440 (3.98).

EXAMPLE 27

A solution of 30g of $NH_3$ in 100 ml of dioxan is added to a solution of 25 g of rifamycin S in 50 ml of dioxan and the whole allowed to stand at 20° C until the initially dark violet reaction mixture has turned a brown-yellow color. The reaction mixture is then treated with 700 ml of water, the pH value adjusted to 7.5–8 with citric acid and then extracted with 300 ml of chloroform. The aqueous phase is discarded, the chloroform phase agitated with an aqueous solution of 50 g of potassium ferricyanide and 10 g of sodium bicarbonate. The chloroform solution is separated off, dried and evaporated. The brown residue is chromatographed on 1500 g of silica gel with ether containing 3% of methanol. 3 Zones are observed: the middle, wine-red zone contains 3-aminorifamycin-S. The eluate of the wine-red middle zone is collected, evaporated and the residue crystallized from ether and then from 90% methanol. Black-violet crystals melting at 171°–172° C are obtained which are 3-amino-rifamycin-S.

EXAMPLE 28

A solution of 25 g of (0.036 mol) of rifamycin-S in 50 ml of dioxan is mixed with 25 g (0.16 mol) of 1,8,8-trimethyl-3-azabicyclo[3,2,1]-oct-3-ane and the mixture allowed to stand at 20° C until the initially deep violet color has changed to orange-yellow. The mixture is treated with water, acidified to pH 5, and extracted with chloroform. After drying and evaporation of the chloroform extract, the evaporation residue is dissolved in aqueous methanol, and the solution treated dropwise with concentrated ascorbic acid solution. After the batch has been allowed to stand for a short while, yellow crystals separate; they are filtered off and recrystallized twice from 80% aqueous methanol. There is obtained in this manner 3-(1',8',8'-trimethyl-3'-azabicyclo[3',2',1']-oct-3'-yl)-rifamycin-SV in the form of crystals which melt at 188°–189° C.

Ultraviolet spectrum in 0.01-N alcoholic hydrochlororic acid, mµ (log ε): 222 (4.49), 295 (4.31), ~ 320 (shoulder), 440 (3.90).

EXAMPLE 29

A solution of 25 g (0.036 mol) rifamycin-S in 50 ml of dioxan is mixed with 25 g (0.17 mol) of 3-phenylpyrrolidine and allowed to stand at 20° C until the initially deep violet-red color of the reaction mixture has changed to orange-yellow. The mixture is then diluted with water, the pH adjusted to 5, and the reaction mixture extracted with chloroform. The chloroformic extract is evaporated and the residue dissolved in aqueous methanol, reduced by the addition of 5 g of ascorbic acid, then treated with sodium chloride solution, and again extracted with chloroform. The evaporation residue of this chloroformic extract is chromatographed on 2 kg of acid-washed silica gel, using chloroform+ 1% methanol as eluant. Apart from a dark, fixed top zone, two bands are observed. The eluate of the wider band, which travels faster, is collected and evaporated. The evaporation residue consists of pure 3-(3'-phenylpyrrolidino)-rifamycin-SV.

Ultraviolet spectrum in 0.01-N alcoholic hydrochloric acid, mµ (log ε): 215 (4.53), 290 (4.26), ~ 320 (shoulder), 440 (4.03).

EXAMPLE 30

A solution of 25 g (0.036 mol) of rifamycin-S in 50 ml of dioxan is mixed with 25 g (0.22 mol) of 3,3-dimethylpiperidine and allowed to stand at 20° C until the initially deep violet-red color of the reaction mixture has changed to orange-yellow. The batch is diluted with water, the pH adjusted to 5, and the mixture extracted with chloroform. The chloroformic extracts are evaporated and the residue dissolved in aqueous methanol, the solution reduced by adding ascorbic acid, then treated with sodium chloride solution, and again extracted with chloroform. The evaporation residue of this chloroformic extract is chromatographed on 2 kg of acid-washed silica gel, using chloroform+ 1% methanol as eluant. Apart from a dark, fixed top zone, two bands are observed. The eluate of the wider band, which travels faster, is collected and evaporated. From the aqueous, methanolic solution of the evaporation residue 3-(3',3'-dimethylpiperidino)-rifamycin-SV crystallizes in the form of yellow crystals which melt with decomposition at 254°–256° C.

Ultraviolet spectrum in 0.01-N alcoholic hydrochloric acid, mµ (log ε): 221 (4.45), 296 (4.17), ~ 320 (shoulder), 444 (3.86).

EXAMPLE 31

A solution of 25 g (0.036 mol) of rifamycin-S in 50 ml of dioxan is mixed with 25 g (0.13 mol) of 3-ethyl-3-phenyl-piperidine and the mixture allowed to stand at 20° C until the initially deep violet-red color of the reaction mixture has changed to orange-yellow. The mixture is diluted with water, the pH adjusted to 5, and the mixture extracted with chloroform. The chloroformic extract is evaporated and the residue dissolved in aqueous methanol, the solution is reduced by adding 5 g of ascorbic acid, then treated with sodium chloride solution, and extracted again with chloroform. The chloroformic extract is evaporated and the residue chromatographed over 2 kg of acid-washed silica gel using chloroform+ 1% methanol as eluant. Apart from for a dark, fixed top zone, two bands are observed. The eluate of the wider band, which travels faster, is collected and evaporated. The residue consists of pure 3-(3'-ethyl-3'-phenylpiperidino)-rifamycin-SV.

Ultraviolet spectrum in 0.01-N alcoholic hydrochloric acid, mµ (log ε): 209 (4.61), ~ 230 (shoulder), ~ 280 (shoulder) 320 (4.10), 440 (3.76).

EXAMPLE 32

A solution of 25 g (0.036 mol) of rifamycin-S in 50 ml of dioxan is mixed with 25 g (0.13 mol) of 3-ethyl-3- cyclohexyl-piperidine and allowed to stand at 20° C until the initially deep violet-red color of the reaction mixture has changed to orange-yellow. The mixture is diluted with water, the pH adjusted to 5, and the reaction mixture then extracted with chloroform. The chloroformic extract is evaporated and the residue dissolved in aqueous methanol, reduced by adding 5 g of ascorbic acid, then mixed with sodium chloride solution, and again extracted with chloroform. The chloroformic extract is evaporated and the residue chromatographed over 2 kg of acid-washed silica gel, using chloroform+ 1% methanol as eluant. Apart from a dark, fixed top zone, two bands are observed. The eluate of the wider band, which travels faster, is collected and evaporated. The residue consists of pure 3-(3'-ethyl-3'-cyclohexylpiperidino)-rifamycin-SV.

Ultraviolet spectrum in 0.01-N alcoholic hydrochloric acid, m$\mu$ (log $\epsilon$): 209 (4.55), $\epsilon$ 225 (shoulder), 262 (4.37), 320 (4.10), ~ 430 (shoulder).

EXAMPLE 33

A solution of 10 g (0.014 mol) of 16,17,18,19,28,29-hexahydrorifamycin-S in 20 ml of dioxan is mixed with 10 g (0.79 mol) of 4-isopropylpiperidine and the mixture allowed to stand overnight at 20° C. It is then treated with water, the pH adjusted to 5, and the mixture extracted with chloroform. The chloroformic extract is vigorously stirred for some time with an excess aqueous solution of potassium ferricyanide rendered alkaline with sodium bicarbonate; it is then acidified, and the chloroform phase is separated. The chloroformic extract is evaporated and the residue chromtographed on 1000 g of silica gel impregnated with triethylamine. Ether containing 1% of methanol is used as eluant. In addition to other bands, a rapidly travelling violet band is observed. The eluate of this rapid band is evaporated, the residue dissolved in methanol, and the methanolic solution treated with aqueous methanolic ascorbic acid until the initially violet color of the solution has turned yellow. The yellow solution is mixed with sodium chloride solution and extracted with chloroform. After drying and evaporation of the chloroformic extract a residue is obtained which is dissolved in methanol. When the solution is allowed to stand, 16,17,18,19,28,29-hexahyro-3-(4'-isopropyl-piperidino)-rifamycin-SV crystallizes. Melting point, 175°–176° C.

Ultraviolet spectrum in 0.01-N alcoholic hydrochloric acid, m$\mu$ (log $\epsilon$): 214 (4.38), 234 (4.56), 300 (4.29), ~ 315 (shoulder), 440 (3.95).

EXAMPLE 34

A solution of 25 g (0.036 mol) of rifamycin-S in 50 ml of dioxan is mixed with 25 g (0.22 mol) of 4-ethyl-piperidine and the mixture allowed to stand at 20° C until the initially deep violet color of the reaction mixture has changed to orange-yellow. The mixture is treated with water, acidified to pH 5, and extracted with chloroform. The chloroformic extract is dried and evaporated, and the residue dissolved in aqueous methanol and treated dropwise with concentrated ascorbic acid solution. When the solution is allowed to stand for a short time, yellow crystals separate, which are filtered off and recrystallized twice from 80% aqueous methanol. There is obtained in this manner 3-(4'-ethyl-piperidino)-rifamycin-SV in the form of crystals which melt at 173° C.

Ultraviolet spectrum in 0.01-N alcoholic hydrochloric acid, m$\mu$ (log $\epsilon$): 220 (4.56), 295 (4.29), ~ 320(shoulder), 445 (3.99).

EXAMPLE 35

A solution of 25 g (0.036 mol) of rifamycin-S in 50 ml of dioxan is treated with 25 g (0.16 mol) of 3-azas-piro-[5.5]-undecane, and then allowed to stand at 20° C until the initially deep violet-red color of the reaction mixture has changed to orange-yellow. The mixture is diluted with water, adjusted to pH 5, and extracted with chloroform. The chloroformic extract is evaporated and the residue dissolved in aqueous methanol, and reduced by adding 5 g of ascorbic acid, then treated with sodium chloride solution, and again extracted with chloroform. The chloroformic extract is evaporated and the residue chromatographed on 2 kg of acid-washed silica gel, using chloroform+ 1% methanol as eluant. Apart from a dark, fixed top zone, two bands are observed. The eluate of the wider band, which travels faster, is collected and evaporated. The residue consists of pure 3-(azaspiro-[5'.5']-undec-3'-yl)-rifamycin-SV.

Ultraviolet spectrum in 0.01-N alcoholic hydrochloric acid, m$\mu$ (log $\epsilon$): 220 (4.56), 296 (4.24), ~ 320 (shoulder) 443 (3.96).

EXAMPLE 36

A solution of 25 g (0.036 mol) of rifamycin-S in 50 ml of dioxan is treated with 25 g (0.18 mol) of 8-azaspiro-[4,5]-decane and allowed to stand at 20° C until the initially deep violet-red color of the reaction mixture has turned orange-yellow. The batch is diluted with water, the pH adjusted to 5, and the mixture extracted with chloroform. The chloroformic extract is evaporated and the residue dissolved in aqueous methanol, reduced by adding 5 g of ascorbic acid, then treated with sodium chloride solution, and again extracted with chloroform. The chloroformic extract is evaporated and the residue chromatographed on 2 kg of acid-washed silica gel, using chloroform+ 1% methanol as eluant. Apart from a dark, fixed top zone, two bands are observed. The eluate of the wider band, which travels faster, is collected and evaporated. The residue consists of pure 3-(8'-azaspiro-[4',5']-dec-8'-yl)-rifamycin-SV.

Ultraviolet spectrum in 0.01-N alcoholic hydrochloric acid, m$\mu$ (log $\epsilon$): 224 (4.54), 295 (4.24), ~ 320 (shoulder), 443 (3.96).

EXAMPLE 37

A solution of 25 g (0.036 mol) of rifamycin-S in 50 ml of dioxan is treated with 25 g (0.16 mol) of 3-cyclohexylpyrrolidine and allowed to stand at 20° C until the initially deep violet-red color of the reaction mixture has changed to orange-yellow. The mixture is then diluted with water, the pH adjusted to 5, and the mixture extracted with chloroform. The chloroformic extract is evaporated and the residue dissolved in aqueous methanol, the solution reduced by adding 5 g of ascorbic acid, then treated with sodium chloride solution, and extracted again with chloroform. The chloroformic extract is evaporated and the residue chromatographed on 2 kg of acid-washed silica gel, using chloroform+ 1% methanol as eluant. In addition to a dark, fixed top zone, two bands are observed. The eluate of the wider band, which travels faster, is collected and evaporated. The residue consists of pure 3-(3'-cyclohexyl-pyrrolidino)-rifamycin-SV.

Ultraviolet spectrum in 0.01-N alcoholic hydrochloric acid, mμ (log ε): 225 (4.53), 284 (4.24), ~ 315 (shoulder), 440 (4.04).

EXAMPLE 38

A solution of 3.5 g (0.005 mol) of rifamycin-S in 10 ml of dioxan is treated with 4 g (0.032 mol) of 3-azabicyclo[3,3,1]nonane and allowed to stand at 20° C until the initially deep violet-red color of the reaction mixture has changed to orange-yellow. The batch is then diluted with water, the pH adjusted to 5, and the reaction mixture then extracted with chloroform. The chloroformic extract is evaporated and the residue dissolved in aqueous methanol, the solution reduced by adding ascorbic acid, then treated with sodium chloride solution and again extracted with chloroform. The chloroformic extract is evaporated and the residue chromatographed on 400 g of acid-washed silica gel, using chloroform+ 1% methanol as eluant. Apart from a dark, fixed top zone, two bands are observed. The eluate of the wider band, which travels faster, is collected and evaporated. When the aqueous-methanolic solution of the evaporation residue is allowed to stand, 3-(3'-azabicyclo[3',3',1']non-3'-yl)-rifamycin-SV crystallizes out forming yellow crystals of melting point 168°–170° C.

Ultraviolet spectrum in 0.01-N alcoholic hydrochloric acid, mμ (log ε): 218 (4.56), 296 (4.28), ~ 320 (shoulder), 438 (3.90).

EXAMPLE 39

10 g of rifamycin-S are dissolved in 30 ml of 1,2,3,4-tetrahydroisoquinoline. The solution is allowed to stand at 25° C until the color changes, then dissolved in a 5:1-mixture of ether and chloroform, after which all tetrahydroisoquinoline is extracted by agitation with citric acid solution. The organic phase is then evaporated, the residue reduced in the usual manner with ascorbic acid, and chromtographed on 1000 g of acid-washed silica gel. Chloroform is used as eluant. Three yellow bands are observed. The eluate of the band which eluates most slowly is evaporated; the residue crystallizes from aqueous methanol. 3-(1',2',3',4'-tetrahydroisoquinol-2'-yl)-rifamycin-SV is obtained in the form of yellow crystals melting at 175° C.

EXAMPLE 40

A solution of 25 g (0.036 mol) of rifamycin-S in 50 ml of dioxan is mixed with 25 g (0.22 mol) of 3-ethylpiperidine and the mixture allowed to stand at 20° C until the initially deep-violet-red color of the reaction mixture has changed to orange-yellow. The mixture is diluted with water, the pH adjusted to 5, and the mixture extracted with chloroform. The chloroformic extract is evaporated and the residue dissolved in aqueous methanol, the solution reduced with 5 g of ascorbic acid, then treated with sodium chloride solution, and again extracted with chloroform. The chloroformic extract is evaporated and the residue chromatographed on 2 kg of acid-washed silica gel using chloroform+ 1% methanol as eluant. Apart from a dark, fixed top zone, two bands are observed. The eluate of the faster travelling, wider band is collected and evaporated. The residue consists of pure 3-(3'-ethyl-piperidino)-rifamycin-SV which crystallizes from ether and, after recrystallization from 80% methanol, melts at 167° C.

Ultraviolet spectrum in 0.01-N alcoholic hydrochloric acid, mμ (log ε): 216 (4.46), 270 (4.48), 326 (4.15), 550 (3.38).

EXAMPLE 41

A solution of 25 g (0.036 mol) of rifamycin S in 50 ml of dioxane is mixed with 20 ml (0.2 mol) of 3-methylpiperidine and left to stand at 20° C until the reaction mixture, which is initially a deep violet colour, has assumed an orange-yellow colour. The reaction mixture is now diluted with water, acidified to pH 5 and extracted with chloroform. After drying and evaporation of the chloroform extract, the evaporation residue is dissolved in methanol and mixed dropwise wise with concentrated ascorbic acid solution. After standing for some time yellow crystals deposit and these are filtered off and twice recrystallised from 80 % strength aqueous methanol. The 3-(3'-methylpiperidino)-rifamycin SV is thus obtained in coarse prisms of melting point 260° C (decomposition).

Ultraviolet spectrum in 0.01 N alcoholic HCl, mμ (log ε): 260 (4.43), 315(4.44), 565(3.55).

Potassium ferricyanide oxidises the compound to a violet-red quinone of melting point (decomposition): 224° C (from 80 % methanol/water). Ultraviolet spectrum in $C_2H_5OH$, mμ (log ε): 222 (4.50), 274 (4.47); 327 (4.19), 550 (3.45).

EXAMPLE 42

A solution of 25 g (0.036 mol) of rifamycin S in 50 ml of dioxane is mixed with 20 ml (0.2 mol) of 4-methylpiperidine and left to stand at 20° C until the reaction mixture, which is initially deep violet in colour has assumed an orange-yellow colour. The reaction mixture is now diluted with water, acidified to pH 5 and extracted with chloroform. After drying and evaporating the chloroform extract, the evaporation residue is dissolved in methanol and mixed dropwise with concentrated ascorbic acid solution. After standing for some time yellow crystals separate out and are filtered off and twice recrystallised from 80 % strength aqueous methanol. 3-(4-methylpiperidino)-rifamycin SV is thus obtained in crystals of melting point 185°–186° C.

Ultraviolet spectrum in 0.01 N alcoholic HCl, mμ (log ε): 224(4.59), 295(4.29), 444 (4.04).

Potassium ferricyanide oxidises the compound to a violet quinone. Ultraviolet spectrum: mμ (log ε): 219(4.41), 270 (4.40), 324(4.12), 550(3.32).

EXAMPLE 43

25 g (0.036 mol) of rifamycin S, 25 ml of dioxane and 25 g (0.28 mol) of 3,4-dimethylpiperidine (obtained by catalytic hydrogenation of 3,4-lutidine) are mixed and left to stand overnight at 20° C. The reaction mixture, which after this time is orange-yellow in colour, is mixed with water and acidified to pH 5. A material (25 g) consisting of two components can be isolated therefrom with chloroform. (Thin layer chromatogram on citric acid-impregnated silica gel, running agent chloroform with 1% methanol).

For separation into the constituents, the material obtained by chloroform extraction is chromatographed on 2000 g of acid-washed silica gel; chloroform with 1% methanol serves as the eluting agent.

2 bands are observed, the eluates of which are collected separately. The eluate of the band first eluted on evaporation leaves a light yellow residue which crystallises from hot 90% strength aqueous methanol. The crystals which melt at 238° C (decomposition) represent one of the epimeric 3-(3',4'-dimethylpiperidino)-rifamycin SV compounds.

Ultraviolet spectrum in 0.01 N alcoholic HCl, mμ (logε): 220 (4.55), 315 (4.18), 444 (3.92).

The NMR-spectrum, CCl$_3$, in the region above δ = 10 only shows the signals for NHCO (10.34) and for 3 phenolic OH (11.50, 12.82 and 13.82). The crude product obtained from the second band which is separated off consists of material which is not yet pure and is therefore again chromatographed over 2000 g of silica gel as previously. After separating off a quantity of the more rapidly migrating epimer of melting point 238° C, the more slowly migrating isomer of 3-(3',4'-dimethylpiperidino)-rifamycin SV is eluted; this crystallises from 80% strength aqueous methanol and melts at 171°–173° C.

Ultraviolet spectrum in 0.01 N alcoholic HCl, mμ (logε): 220 (4.50), 271 (4.43), 324 (4.16), ~ 440 (shoulder).

EXAMPLE 44

25 g (0.036 mol) of rifamycin S, 25 ml of dioxane and 25 g (0.28 mol) of 3,5-dimethylpiperidine (obtained by catalytic hydrogenation of 3,5-lutidine) are mixed and left to stand overnight at 20° C. The reaction mixture, which after this time is orange-yellow in colour, is mixed with water, acidified to pH 5 and extracted with chloroform. The chloroform extract is stirred for half an hour with an excess of aqueous potassium ferricyanide solution rendered alkaline with bicarbonate, and is then acidified with citric acid and the dark-coloured chloroform phase is separated off. The residue remaining after drying and evaporation of the chloroform phase is crystallised from ether and thereafter again crystallised from aqueous methanol. 3-(3',5'-dimethylpiperidino)-rifamycin S is thus obtained in black-violet glossy crystals of melting point 233° C (decomposition).

Ultraviolet spectrum (ethanol), mμ (logε): 227 (4.48), 268 (4.48), 324 (4.20), 550 (3.48).

Infrared spectrum (methylene chloride): 3500,3430 (OH,NH), 1735 (11-C=O), 1715(25-COCOCH$_3$), 1675(4-C=O), 1620(1-C=O and NHCO) cm$^{-1}$.

3-(3'5'-Dimethylpiperidino)-rifamycin SV is obtained from this compound by reduction with ascorbic acid.

EXAMPLE 45

A solution of 25 g (0.036 mol) of rifamycin S in 50 ml of dioxane is mixed with 25 g (0.28 mol) of 4,4-dimethylpiperidine and left to stand overnight at 20° C. Thereafter the reaction mixture is mixed with water, adjusted to pH 5 and extracted with chloroform. The chloroform extract is vigorously stirred for half an hour with an excess of an aqueous potassium ferricyanide solution rendered alkaline with bicarbonate; thereafter the mixture is acidified and the chloroform phase separated off. After evaporation of the chloroform the residue is chromatographed on 2000 g of silica gel using chloroform containing 5% of acetone as the eluting agent. A rapidly migrating dark violet band is separated off, and the eluate of this leaves 3-(4'4'-dimethylpiperidino)-rifamycin S after evaporation.

Ultraviolet spectrum in ethanol, mμ (logε): 270(4.42), 324 (4.12), 550(3.35).

Infrared spectrum in methylene chloride, cm$^{-1}$: 3700,3500 (NH,OH), 1738(11-C=O) 1715(25-COCOCH$_3$), 1670 (4-C=O), 1620 (1-C=O and NHCO).

In order to manufacture the hydroquinone, a methanolic solution of 3-(4',4'-dimethylpiperidino)-rifamycin S is treated dropwise with concentrated aqueous sodium ascorbate solution until the initially dark violet colour of the solution has completely changed to orange yellow. The mixture is diluted with water, adjusted to pH 5 and extracted with chloroform.

The material which remains after evaporation of the chloroform extract crystallises from aqueous methanol. The yellow crystals begin to melt in an unsharp manner at 130° C.

Ultraviolet spectrum in 0.01 N alcoholic HCl, mμ (logε): 220(4.42), 273(4.45), 329(4.13), 550(3.34).

EXAMPLE 46

A solution of 25 g (0.036 mol) of rifamycin S in 50 ml of dioxane is mixed with 15 g (0.18 mol) of 3-methylpyrrolidine and heated for 40 minutes on a boiling water bath. After cooling, the reaction mixture is mixed with water, adjusted to pH 5 and extracted with chloroform. The chloroform extract is evaporated, and the residue is dissolved in methanol and treated dropwise with concentrated aqueous sodium ascorbate solution until the solution has become light orange yellow. Thereafter the mixture is acidified, diluted with water and again extracted with chloroform. The evaporation residue of the chloroform extract is chromatographed on 2000 g of acid-washed silica gel using chloroform as the eluting agent. Two bands are observed. The eluate of the first band is collected and evaporated. The residue crystallises from 80% strength aqueous methanol. After crystallising twice, 3-(3'-methylpyrrolidino)-rifamycin SV of melting point 192°–193° C is obtained in orange-yellow coarse crystals.

Ultraviolet spectrum in 0.01 N alcoholic HCl, mμ (logε): 227(4.57), 290(4.26), 444(4.06).

EXAMPLE 47

A solution of 25 g (0.036 mol) of rifamycin S in 50 ml of dioxane is mixed with 25 g (0.2 mol) of 4-isopropylpiperidine and left to stand at 20° C until the reaction mixture which is initially deep violet in colour has assumed an orange-yellow colour. The reaction mixture is now diluted with water, acidified to pH 5 and extracted with chloroform. After drying and evaporating the chloroform extract, the evaporation residue is dissolved in aqueous methanol containing 5 g of ascorbic acid and left to stand. After some time 3(4'-isopropylpiperidino)-rifamycin SV crystallises in light yellow crystals which after recrystallisation from 90% strength aqueous methanol melt at 175°–177° C.

Ultraviolet spectrum in 0.01 N alcoholic hydrochloric acid, mμ (logε): 222(4.54), 315(4.17), 445(3.90).

EXAMPLE 48

A solution of 25 g (0.036 mol) of rifamycin S in 50 ml of dioxane is mixed with 25 g (0.18 mol) of 4-tert-butylpiperidine and left to stand at 20° C until the reaction mixture which is initially deep violet in colour has assumed an orange-yellow colour. The reaction mixture is now diluted with water, acidified to pH 5 and extracted with chloroform. After drying and evaporation of the chloroform extract, the evaporation residue is dissolved in aqueous methanol containing 5 g of ascorbic acid and is left to stand. After a short time 3-(4-tert. butylpiperidino)-rifamycin SV crystallises; it melts at 185° C after recrystallisation from methanol.

Ultraviolet spectrum in 0.01 N alcoholic hydrochloric acid, mμ (logε): 221(4.54), 290(4.28), 442(3.94).

EXAMPLE 49

A solution of 25 g (0.036 mol) of rifamycin S in 50 ml of dioxane is mixed with 25 g (0.2 mol) of cis-octahydroisoindole and left to stand at 20° C until the reaction mixture which is initially deep violet in colour has assumed an orange-yellow colour. The coloured reaction mixture is now diluted with water, acidified to pH 5 and extracted with chloroform. After drying and evaporating the chloroform extract, the residue is reduced in aqueous methanol by adding 5 g of ascorbic acid and is thereafter mixed with sodium chloride solution and again extracted with chloroform. The evaporation residue of this chloroform extract is chromatographed on 2 kg of silica gel, using chloroform as the eluting agent. Of the two bands which are observed, the eluate of the more rapidly migrating broader band is collected. The residue remaining after evaporation of the eluate is 3-(octahydroisoindol-2'-yl)-rifamycin SV.

Ultraviolet spectrum in 0.01 N alcoholic hydrochloric acid, mμ (logε): 225(4.53), shoulder at 280, 315 (4.13), 445(3.98). The 3-(octahydroisoindol-2'-yl)-rifamycin S which can be manufactured from 3-(octahydroisoindol-2'-yl)-rifamycin SV by oxidation with potassium ferricyanide in a known manner has the following ultraviolet spectrum in ethanol, mμ (logε): 262 (4.42), 327 (4.13), 550 (3.20), infrared spectrum in $CH_2Cl_2$, cm$^{-1}$: 3480(OH), 3420(N$\underline{H}$-CO), 1730(11-C=O), 1715 (Sch, 25-COOC$CH_3$), 1670 (4-CO), 1620(1-CO and NH$\underline{CO}$).

EXAMPLE 50

A solution of 25 g (0.036 mol) of rifamycin S in 50 ml of dioxane is mixed with 25 g (0.2 mol) of 3-ethyl-4-methylpiperidine (obtained by $Pt_2$-hydrogenation of β-collidine in 5 N hydrochloric acid) and left to stand at 20° C until the reaction mixture which is initially deep violet red in colour has assumed an orange-yellow colour. The reaction mixture is now diluted with water, adjusted to pH 5 and extracted with chloroform. The chloroform solution is vigorously stirred for 30 minutes with an excess of aqueous potassium ferricyanide solution rendered alkaline with bicarbonate, and is thereafter separated off, dried and evaporated. The residue is chromatographed on 2 kg of silica gel rendered alkaline by impregnation with triethylamine, using chloroform as the eluting agent and protecting against light. A slowly migrating band of a red colour and a rapidly eluted band of a violet colour are observed. The eluate of the latter is evaporated to dryness, the residue is taken up in methanol and the methanol solution is treated with aqueous-methanolic ascorbic acid solution until the initially violet colour of the solution has changed to yellow. The yellow solution is mixed with sodium chloride solution and extracted by shaking with chloroform. After drying and evaporating the chloroform, a residue remains and after dissolving this in 90% strength aqueous ethanol 3-(4'-methyl-3'-ethylpiperidino)-rifamycin SV crystallises out in coarse crystals of melting point 170°–73° C.

Ultraviolet spectrum in 0.01 N alcoholic hydrochloric acid, Mμ (logε): 224 (4.56), 293(4.28), 320 (shoulder), 443(3.99). NMR spectrum (CDCl₃): between δ =0.5 and δ =1.10 4 $\underline{CH_3}$ CH groups as well as 1 $\underline{CH_3}$ $CH_2$ group (= 15 H) can be detected. A further $\underline{CH_3}$ CH group is present with a higher field, and the absence of doubling in the case of the sharp singlet signals with a low field (3 phenolic O$\underline{H}$, at δ = 11.50, 12.81 and 13.75 as well as N$\underline{H}$ at δ = 10.18) indicates the presence of a sterically homogeneous compound.

EXAMPLE 51

A solution of 25 g (0.036 mol) of rifamycin S in 50 ml of dioxane is mixed with 20 g (0.2 mol) of 3,3-dimethylpyrrolidine and left to stand at 20° C until the reaction mixture which is initially deep violet red in colour has assumed an orange yellow colour. The reaction mixture is now diluted with water, adjusted to pH 5 and extracted with chloroform. After evaporation of the chloroform extract the residue is dissolved in aqueous methanol, reduced by adding 5 g of ascorbic acid, then mixed with sodium chloride solution and again extracted with chloroform. The evaporation residue of this chloroform extract is chromatographed on 2 kg of silica gel using chloroform as the eluting agent. In addition to a dark fixed top zone two bands are observed. The eluate of the more rapidly migrating broader band is collected and evaporated. The evaporation residue consists of pure 3- (3',3'-dimethylpyrrolidino)-rifamycin SV. Ultraviolet spectrum in 0.01 N alcoholic hydrochloric acid, mμ (logε): 223 (4.55), 290 (4.23), 320 (shoulder), 445 (3.99). NMR-spectrum CDCL₃); weak non-equivalence of the two 3',3'-methyl groups (each in a singlet at δ = 1.09 and 1.11). Infrared spectrum ($CH_2Cl_2$), cm$^{-1}$: 3500, 3180, 1730 (shoulder), 1715, 1650, 1590, 1570, 1535 etc.

EXAMPLE 52

A solution of 25 g (0.036 mol) of rifamycin S in 50 ml of dioxane is mixed with 23 g (0.2 mol) of octahydroazocine and left to stand at 20° C until the reaction mixture which is initially deep violet in colour has assumed an orange-yellow colour. The reaction mixture is now diluted with water, adjusted to pH 5 and extracted with chloroform. After drying and evaporating the chloroform extract, the evaporation residue is dissolved in aqueous methanol containing 5 g of ascorbic acid and is left to stand. After some time the 3-(octahydroazocin-1'-yl)-rifamycin SV crystallises in yellow crystals which after recrystallisation from aqueous methanol melt at 206°–207° C. Ultraviolet spectrum in 0.01 N alcoholic hydrochloric acid, mμ (logε): 220(4.59), 295(4.05), 320(shoulder), 440(3.94).

EXAMPLE 53

A solution of 25 g (0.036 mol) of rifamycin S in 50 ml of dioxane is mixed with 32 g (0.2 mol) of 4-phenylpiperidine and left to stand at 20° C until the reaction mixture which is initially deep violet in colour has assumed an orange-yellow colour. The reaction mixture is now diluted with water, acidified to pH 5 and extracted with chloroform. After drying and evaporating the chloroform extract, the evaporation residue is dissolved in aqueous methanol containing 5 g of ascorbic acid and left to stand. After a short time 3-(4'-phenylpiperidino)-rifamycin SV separates out in a crystalline form. The light yellow crystals melt at 211°–212° C after recrystallisation from methanol. Ultraviolet spectrum in 0.01 N alcoholic hydrochloric acid, mμ (logε): 213(4.62), 290 (4.32), 320 (shoulder), 440(3.93).

EXAMPLE 54

A solution of 25 g (0.036 mol) of rifamycin S in 50 ml of dioxane is mixed with 33 g (0.2 mol) of 4-cyclohexylpiperidine and left to stand at 20° C until the reaction mixture which is initially deep violet in colour has assumed an orange-yellow colour. The reaction mixture is now diluted with water, acidified to pH 5 and extracted with chloroform. After drying and evaporating the chloroform extract, the evaporation residue is dissolved in aqueous methanol, containing 5 g of ascorbic acid and is left to stand. 3-(4'-Cyclohexyl-piperidino)-rifamycin SV immediately separates out in a crystalline form. After recrystallisation from methanol the light yellow crystals melt at 188° C.

EXAMPLE 55

Pharmaceutical preparations containing 3-(4'-isopropylpiperidino)-rifamycin SV as an antibiotic for parenteral administration:

100 mg of 3-(4'-isopropylpiperidino)rifamycin SV in the form of the sodium salt are dissolved in 1 ml of distilled water. This solution is lyophilised at −30° C. The dry product thus obtained is used for the manufacture of injection solutions by dilution, for example with 50 ml of distilled water or 100 ml of physiological sodium chloride solution.

EXAMPLE 56

Pharmaceutical preparations containing 3- (3'5'-dimethyl-piperidino)-rifamycin SV as the antibiotic in the form of push-fit capsules.

EXAMPLE 57

10 ml of methoxyethylamine is added to a solution of 10 g of rifamycin S in 30 ml of dioxane and the mixture is allowed to stand 45 minutes at room temperature. The mixture is then acidified with aqueous citric acid and extracted with chloroform. The chloroform solution is then oxidised with potassium ferricyanide solution as described for instance in Example 45. After having evaporated the chloroform the residue is chromatographed on 400 g of silicagel using chloroform. The eluate corresponding to the brown-reddish band moving swiftly is collected and evaporated. The residue when recrystallized from ether yields 3-($\beta$-methoxyethylamino)-rifamycin S, which after two recrystallizations from 10% — aqueous methanol melts at 242° – 244° (under decomposition).

EXAMPLE 58

The 3-amino rifamycin S or SV compounds listed in the table below are prepared starting from rifamycin S and reacting it with the amine listed inthe table according to the following general methods:

10 g of the amine is added to a solution of 10 g of rifamycin S in 30 ml of dioxan at room temperature. The mixture which has assumed a deep red coloration is allowed to stand until the red coloration has changed to yellow-brown. The mixture is then acidified with aqueous citric acid and the reaction product formed is extracted with chloroform after having added such water. The chloroform extract contains the desired 3-amino-rifamycin compound in the quinone and the hydroquinone form and rifamycin SV, as well as variable quantities of resinous material.

a. If the 3-amino-rifamycin compound is to be isolated in the quinone form, the chlorofomr extract is oxidised with an aqueous solution of potassium ferricyanide as described in Example 45. The oxidised material contains the desired 3-amino compound together with rifamycin S. The 3-amino rifamycin S derivative can be obtained in pure form from the residue of this extract by crystallization from ether, aqueous tetrahydrofuran or aqueous methanol or methanol or by chromatography on silicagel using chloroform acetone as eluting agent.

b. If the 3-amino-rifamycin compound is to be isolated in the hydroquinone form, the chloroform extract is evaporated to dryness, the residue is taken up in methanol and an excess of an aqueous sodium ascorbate solution is added, immediate reduction thus taking place. The reaction mixture is then acidified with citric acid and much water is added. It is then extracted with chloroform. The chloroform solution contains the 3-amino-rifamycin compound in the hydroquinone form besides rifamycin SV. From the residue obtained by evaporating the chloroform extract, the 3-amino rifamycin SV compound is obtained in pure form by crystallization from methanol, ethanol, or mixtures of these alcohols with water or by chromatography or silicagel using chloroform/acetone as eluting agent

| 3-Amino derivative of rifamycin S (quinone form = Q) or of rifamycin SV (hydroquinone form = HQ) derived from: | Q or HQ | melting point | UV spectrum nm (log $\epsilon$) Q in $C_2H_5OH$ HQ in 0,01 alc. HCl | | | | |
|---|---|---|---|---|---|---|---|
| diethanolamine | HQ | 189° | 223 (4,60) | 295 (4,33) | 435 (4,00) | | |
| methylaminoacetaldehyde-dimethylacetal | Q | 206° does | 223 (4,50) 260 | 265 (4,45) 322 | 319 (4,22) 380 | ~ 375 (shoulder) 490 | 550 (3,08) |
| 2-diethylaminoethylamine | Q | not melt up to 320° | (4,57) | (4,47) | (3,75) | (3,57) | |
| 2-methyl-piperidine | Q | 211–212° | ~ 243 (shoulder) 213 | 269 (4,56) ~ 230 | 324 (4,18) 295 | 527 (3,56) ~ 320 | 443 |
| 4-benzyl-piperidine | HQ | 159–160° | (4,61) 223 | (shoulder) 296 | (4,28) ~ 320 | (shoulder) 444 | (4,00) |
| 4-(cyclohexylmethyl)-piperidine | HQ | 174° | (4,59) 225 | (4,28) 296 | (shoulder) ~ 325 | (4,03) 444 | |
| 4-(3-cyclohexylpropyl)-piperidine | HQ | 151–153° | (4,58) 225 | (4,28) 297 | (shoulder) ~ 325 | (4,03) 442 | |
| 4-(dicyclohexylmethyl)-piperidine | HQ | 180–185° | (4,50) 220 | (4,28) 295 | (shoulder) ~ 320 | (3,96) 442 | |
| 4-hydroxy-piperidine | HQ | 205–206° | (4,60) 223 | (4,28) 295 | (shoulder) ~ 320 | (3,95) 442 | |
| 4-hydroxymethyl-piperidine | HQ | 208–209° | (4,40) 222 | (4,12) ~ 280 | (shoulder) ~ 325 | (3,81) 440 | |
| piperidine-4-carboxylic-acidamide | HQ | 202° | (4,53) | (shoulder) | (shoulder) | (3,86) | |

-continued

| 3-Amino derivative of rifamycin S (quinone form = Q) or of rifamycin SV (hydroquinone form = HQ) derived from: | Q or HQ | melting point | UV spectrum nm (log ε) Q in $C_2H_5OH$ HQ in 0,01 alc. HCl | | | | |
|---|---|---|---|---|---|---|---|
| 2,6-dimethylmorpholine | Q | 240° | 222 (4,47) | 272 (4,43) | 323 (4,18) | ~ 390 (shoulder) | 550 (3,45) |
| 2,6-dimethyl-thiomorpholine | HQ | 243–245° | 220 (4,55) | 282 (4,32) | ~ 320 (shoulder) | 440 (3,89) | |
| piperazine | HQ | does not melt up to 225 | (4,52) | 295 (4,25) | 435 (3,88) | | |
| 4-methyl-1-azacyclo-heptane | HQ | 200–201° | 220 (4,44) | 293 (4,18) | ~ 320 (shoulder) | 444 (3,88) | |
| 4-t-butyl-1-azacyclo-heptane | HQ | 244° | 223 (4,58) | 294 (4,27) | ~ 320 (shoulder) | 444 (4,01) | |
| (2'-hydroxyethyl)-N'-piperazine | HQ | above 200° | 229 (4,55) | 301 (4,26) | 439 (3,92) | | |
| 2-methoxy-ethylamine | Q | 242–244° | 211 (4,50) | 230 (4,49) | 264 (4,48) | 315 (4,18) | 368 (3,88) | 320 (3,23) |
| 3-methoxy-propylamine | Q | 189° | 213 (4,33) | 232 (4,37) | 263 (4,32) | 315 (4,04) | 365 (3,72) | 520 (3,04) |
| N-methyl-N-β-cyanoethylamine | Q | 183–185° | 233 (4,50) | 265 (4,49) | 317 (4,17) | 367 (3,89) | 520 (3,26) |
| 3-ethoxy-propylamine | Q | 205° | 230 (4,50) | 265 (4,48) | 317 (4,17) | 367 (3,81) | 520 (3,28) |
| N'-phenyl-piperazine | HQ | 186–187° | 229 (4,59) | 295 (4,32) | 440 (3,91) | | |
| N'-ethyl-piperazine | Q | 155–160° | 217 (4,48) | 272 (4,48) | 324 (4,17) | 544 (3,42) | |
| N'-benzyl-piperazine | HQ | 170–172° | 214 (4,58) | 228 (4,57) | 299 (4,29) | 436 (3,90) | |
| β-dimethylamino-ethylamine | Q | melts above 170° | 231 (4,44) | 265 (4,43) | 317 (4,12) | 366 (3,84) | 525 (3,23) |
| 3',4'-dimethoxy-benzylamine | Q | 174° | 232 (4,59) | 267 (4,50) | 317 (4,22) | 365 (3,89) | 520 (3,32) |
| 3',4'-diethyl-benzylamine | Q | 128–130° | 232 (4,58) | 267 (4,48) | 317 (4,18) | 535 (3,28) | |
| 3-amino-1-ethyl-piperidine | Q | amorphous | 230 (4,47) | 268 (4,45) | 318 (4,16) | 368 (3,85) | 530 (3,26) |

EXAMPLE 59

3-[2'-diethylamino-ethylamino]-rifamycin S is dissolved in a solution of methyl iodide in methanol and is allowed to stand several hours at 20° C. The solvent is then evaporated and the residue is reprecipitated from chloroform - ether. There is obtained the methoxiodide of the base used as starting material in amorphous for UV (nm, log ε): 267(4.47), 313(4.20), 365(3.86), 520(shoulder)

In an analogous manner the methiodide of 3-]2'-morpholino - ethylamino]-rifamycin S is obtained in amorphous form starting from rifamycin S and 2- morpholino-ethylamine. UV (nm, log ε): 268(4.47), 313(4.7), 365(3.86), 510(3.20).

EXAMPLE 60

90 g of rifamycin S are dissolved in a mixture of 100 ml of dioxane and 96 g of 1-isobutylpiperazine and the solution is left to stand at room temperature for 28 hours. After this time, water is added, the mixture is acidified with citric acid and the reaction product is taken up with chloroform. The chloroform solution is washed with sodium chloride solution, dried with magnesium sulphate and evaporated. The residue is dissolved in methanol, aqueous concentrated ascorbic acid solution is added dropwise until a light yellow colour is achieved, and the mixture is left to stand. After a short time, 3-(4-isobutyl-1-piperazinyl)-rifamycin SV separates out in yellow crystals which after two recrystallisations from chloroform-methanol-water melt at 170° C. Further quantities are to be found in the last two mother liquors.

UV spectrum in 0.01 N alcoholic HCl, maxima in nm (log ε): 228(4.53), 298(4.28) and 433(3.90).

EXAMPLE 61

Analogously to the description in Example 60, 90 g of rifamycin S are reacted with 100 g of 1-(2-ethylbutyl)-piperazine, and 3-[4-(2-ethylbutyl)-1-piperazinyl]-rifamycin SV is thus obtained.

EXAMPLE 62

Analogously to the description in Example 60, 90g of rifamycin S are reacted with 100 g of 1-(2-methylbutyl)-piperazine, and 3-[4-(2-methylbutyl)-1-piperazinyl]-rifamycin SV is thus obtained.

EXAMPLE 63

Pharmaceutical preparations, in the form of push-fit capsules, containing 3-(4-isobutyl-1-piperazinyl)-rifamycin SV as the antibiotic.

| Composition | |
|---|---|
| 3-(4-Isobutyl-1-piperazinyl)-rifamycin SV | 50.00 mg |
| Lactose | 100.00 mg |
| Ethylcellulose | 1.50 mg |
| Stearic acid | 1.50 mg |
| | 153.00 mg |

Manufacture

1. The active substance is mixed with the lactose.
2. The ethylcellulose is dissolved in a 10-fold quantity of methylene chloride.
3. Mixture (1) is moistened with solution (2) and beaten through a sieve of 3–5 mm mesh width and dried at a temperature not exceeding 40° C.
4. The dry granules are beaten through a sieve of 0.5 mm mesh width and mixed with pulverulent stearic acid. The mixture is then filled into push-fit capsules of size 2.

EXAMPLE 64

30 g of 1-cyclohexylmethylpiperazine are added to a solution of 30 g of rifamycin S in 100 ml of dioxane and the mixture is left to stand at room temperature until the initially violet-blue colour of the reaction mixture has changed to orange-brown. Water is then added and the mixture is acidified with citric acid. The desired reaction product is taken up with chloroform. After drying and evaporating the chloroform solution, the residue which remains is dissolved in a little methanol and concentrated aqueous ascorbic acid solution is added dropwise until the initially dark coloration of the methanol solution has become golden yellow. After brief standing, 3-(4-cyclohexylmethyl-1-piperazinyl)-rifamycin SV crystallises and is obtained completely pure after two recrystallisations from chloroform-methanol-water. Melting point 176°–178° C. The mother liquor of the first crystallisation contains almost exclusively rifamycin SV alongside the desired reaction product.

UV spectrum in 0.01 N alcoholic HCl, maxima in nm (log$\epsilon$): 228(4.53), 298(4.28) and 433(3.90).

EXAMPLE 65

Following an analogous procedure to that described in the preceding example, 25 g of rifamycin S in 40 ml of dioxane with 30 g of 1-cyclopropylmethylpiperazine give 3-(4-cyclopropylmethyl-1-piperazinyl)-rifamycin SV, which after three crystallisations from chloroform-methanol-water is obtained in yellow crystals of melting point 217° C. UV spectrum in 0.01 N alcoholic HCl, maxima in nm (log$\epsilon$): 225(4.54), 272(4.30) and 430(3.81).

EXAMPLE 66

Pharmaceutical preparations, in the form of pushfit capsules, containing 3-(4-cyclohexylmethyl-1-piperazinyl)-rifamycin SV as the antibiotic.

| Composition | |
|---|---|
| 3-(4-Cyclohexylmethyl-1-piperazinyl)-rifamycin SV | 100.00 mg |
| Lactose | 50.00 mg |
| Ethylcellulose | 1.50 mg |
| Stearic acid | 1.50 mg |
| | 153.00 mg |

Manufacture

1. The active substance is mixed with the lactose.
2. The ethylcellulose is dissolved in a 10-fold quantity of methylene chloride.
3. Mixture (1) is moistened with solution (2) and beaten through a sieve of 3–5 mm mesh width and dried at a temperature not exceeding 40° C.
4. The dry granules are beaten through a sieve of 0.5 mm mesh width and mixed with pulverulent stearic acid. The mixture is then filled into push-fit capsules of size 2.

EXAMPLE 67

20 g of rifamycin S are dissolved in a mixture of 100 ml of dioxane and 27 g of N-methallylpiperazine and the solution is left to stand at room temperature for 35 hours. After this time, water is added, the mixture is acidified with citric acid and the reaction product is taken up with chloroform. The chloroform solution is washed with sodium chloride solution, dried over sodium sulphate and evaporated. The residue is dissolved in methanol, aqueous concentrated ascorbic acid solution is added dropwise until a light colour is achieved and the mixture is left to stand. After a short time, 3-(4-methallyl-1-piperazinyl)-rifamycin SV separates out in yellow crystals which after two recrystallisations from chloroform-methanol-water melt at 172°–174° C. Further amounts are to be found in the last two mother liquors.

UV spectrum in 0.01 N alcoholic HCl, maxima in nm (log$\epsilon$): 299 (4.59), 298 (4.31) and 435 (3.90).

EXAMPLE 68

Analogously to the description in Example 67, 10 g of rifamycin S are reacted with 12 g of 1-allylpiperazine and 3-[4-allyl-1-piperazinyl]-rifamycin SV of melting point 174°–177° C is thus obtained.

UV spectrum (recorded as in Example 67):228 (4.60), 297 (4.32) and 435 (3.91).

EXAMPLE 69

Analogously to the description in Example 67, 10 g of rifamycin S are reacted with 10 g of N-(2-methyl-2-pentenyl)-piperazine and 3-[4-(2-methyl-2-pentenyl)-1-piperazinyl]-rifamycin SV of melting point 164°–166° C is thus obtained.

UV spectrum (recorded as in Example 67):228 (4.58), 298 (4.30) and 435 (3.92).

EXAMPLE 70

Analogously to the description in Example 67, 20 g of rifamycin S are reacted with 20 g of N-(2-ethyl-2-butenyl)-piperazine and 3-[4-(2-ethyl-2-butenyl)-1-piperazinyl]-rifamycin SV of melting point 174°–175° C is thus obtained.

UV spectrum (recorded as in Example 67):229 (4.60) 298 (4.33) and 435 (3.93).

EXAMPLE 71

Analogously to the description in Example 67,15 g of rifamycin S are reacted with 16 g of N-(2-ethyl-2-hexenyl)-piperazine and 3-[4-(2-ethyl-2-hexenyl)-1-piperazinyl]-rifamycin SV of melting point 153°–156° C is thus obtained.

UV spectrum (recorded as in Example 8): 229 (4.61), 298 (4.33) and 435 (3.94).

EXAMPLE 72

Analogously to the description in Example 67, 20 g of rifamycin S are reacted with 20 g of N-(2,3-dimethyl-2-butenyl)-piperazine and 3-[4-(2,3-dimethyl-2-butenyl)-1-piperazinyl]-rifamycin SV of melting point 171°–174° C is thus obtained.

UV spectrum (recorded as in Example 67):230 (4.60), 300 (4.33) and 435 (3.93).

EXAMPLE 73

Analogously to the description in Example 67, 10 g of rifamycin S are reacted with 11 g of N-(2-ethylbutyl)-piperazine and 3-[4-(2-ethylbutyl)-1-piperazinyl]-rifamycin SV of melting point 168°–170° C is thus obtained.

UV spectrum (recorded as in Example 67):228 (4.47), 299 (4.32) and 435 (3.94).

EXAMPLE 74

A mixture of 55 ml of ethanol, 1 ml of water, 1.15 g of cyclobutylmethyl bromide (2 equivalents) and 2.5 ml (approx. 2 equivalents) of Hunig's base (ethyl-diisopropylamine) is added to 3 g of 3-(1-piperazinyl)-rifamycin SV and the solution is warmed under reflux for 20 hours. After this time, water is added, the mixture is acidified with citric acid and the reaction product is taken up with chloroform. The chloroform solution is washed with sodium chloride solution, dried with sodium sulphate and evaporated. The residue is dissolved in methanol, a few drops of aqueous concentrated ascorbic acid solution are added and the mixture is left to stand. After a short time 3-(4-cyclobutylmethyl-1-piperazinyl)-rifamycin SV separates out in yellow crystals which after two recrystallisations from chloroform-methanol-water slowly decompose above 195° C. Further quantities are to be found in the last two mother liquors.

UV spectrum in 0.01 N alcoholic HCl, maxima in nm (log ε): 230 (4.58), 299 (4.30) and 435 (3.90).

EXAMPLE 75

Analogously to the description in Example 74, 5 g of 3-(1-piperazinyl)-rifamycin SV are reacted with 2.1 g (2 equivalents) of cyclopentylmethyl bromide and 2.5 ml (2 equivalents) of Hünig base and 3-(4-cyclopentyl-methyl-1-piperazinyl)-rifamycin SV of melting point 180°–185° C (decomposition) is thus obtained.

UV spectrum: 228 (4.58), 298 (4.31) and 435 (3.92) (recorded as in Example 67).

EXAMPLE 76

Analogously to the description in Example 74, 10 g of rifamycin S are reacted with 10 g of N-(1,2-dimethylpropyl)-piperazine and 3-[4-(1,2-dimethylpropyl)-1-piperazinyl]-rifamycin SV of melting point 184°–° C is thus obtained.

UV spectrum: 230 (4,58), 299 (4.33) and 435 (3.93) (reocorded as in Example 67).

EXAMPLE 77

If rifamycin S is reacted in the manner indicated below with the N-substituted piperazines listed in the first column of the table which follows, the rifamycin SV derivatives substituted in the 3-position by the corresponding N'-substituted 1-piperazinyl radical are obtained, which have the physical data listed in the table.

| Reactants | | | Reaction products | |
|---|---|---|---|---|
| Solvent | Rifamycin S | Amine | Melting point | UV in 0.01 N alcoholic HCl, maxima in nm (log ε) |
| 50 ml of dioxane | 25 g | 35 g of N-(2-phenylpropyl)-piperazine | 157–158° C | 226 (459), 298 (4.32), 434 (3.93) |
| 70 ml of dioxane | 25 g | 33 g of N-(2-methylpentyl)-piperazine | 163° C | 229 (4.59), 300 (4.32), 437 (3.93) |
| 70 ml of dioxane | 25 g | 30 g of N-(cycloheptylmethyl)-piperazine | 174° C | 229 (4.59), 299 (4.31), 432 (3.93) |
| 70 ml of dioxane | 25 g | 30 g of N-(3-methylpentyl)-piperazine | 173° C | 226 (4.58), 298 (4.30), 433 (3.90) |
| 70 ml of dioxane | 20 g | 28 g of N-[(3-cyclohexen-1-yl)-methyl]-piperazine | 170–172° C | 228 (4.77), 297 (4.50), 435 (4.09) |
| 100 ml of dioxane | 25 g | 30 g of N-(2-norbornyl-methyl)-piperazine | 162° C | 228 (4.55), 302 (4.27) 440 (3.94) |
| 100 ml of dioxane | 25 g | 30 g of N-(cyclooctylmethyl)-piperazine | 171° C | 227 (4.53), 297 (4.24), 432 (3.82) |
| 70 ml of dioxane | 20 g | 30 g of N-[(2-methylcyclohexyl)-methyl]-piperazine | 169–170° C | |
| 70 ml of dioxane | 20 g | 30 g of N-(2-benzyl-propyl)-piperazine | 149–150° C | 228 (4.57), 299 (4.32) 435 (3.93) |
| 30 ml of dioxane | 6 g | 5.2 g of N-neopentyl-piperazine | 180° C | 227 (4.56), 430 (3.86) ~ 295 (shoulder) |
| 100 ml of dioxane | 30 g | 44 g of N-(3,3-dimethylbutyl)-piperazine | 178° C | |
| 100 ml of dioxane | 30 g | 40 g of N-(3-methylbutyl)-piperazine | 178–179° C | |
| 150 ml of dioxane | 20 g | 27 g of N-(3-phenyl-2-propenyl)-piperazine | 165–166° C | 206 (4.71), 211 (4.73), 230 (4.63), 249 (4.60), 295 (4.32), 435 (3.93) |
| 20 ml of dioxane | 10 g | 10 g of N-phenyl-piperazine | 186–187° C | 229 (4.59), 295 (4.32) 440 (3.92) |
| 30 ml of dioxane | 20 g | 20 g of N-benzyl-piperazine | 170–172° C | 214 (4.58), 228 (4.57) 299 (4.29), 436 (3.90) |
| 100 ml of dioxane | 30 g | 30 g of N-(p-chlorobenzyl)-piperazine | 170–172° C | 223 (4.70), 299 (4.31) 438 (3.92) |
| 100 ml of dioxane | 30 g | 30 g of N-phenetyl-piperazine | 166–167° C | |
| 100 ml of dioxane | 30 g | 30 g of N-(p-methoxy)-piperazine | 171–172° C | 229 (4.69, 299 (4.28), 439 (3.90) |
| 100 ml of dioxane | 30 g | 30 g of N-(p-methylbenzyl)-piperazine | 168–170° C | 220 (4.68), 297 (4.33), 435 (3.93) |
| 20 ml of dioxane | 20 g | 25 g of N-(o-methylbenzyl)-piperazine | 171–173° C | 215 (4.63), 299 (4.31), 436 (3.93) |
| 70 ml of dioxane | 25 g | 39 g of N-(p-isopropylbenzyl)-piperazine | 168–169° C | 221 (4.67), 299 (4.32), 435 (3.93) |
| 70 ml of dioxane | 25 g | 30 g of N-(m-methylbenzyl)-piperazine | 166–167° C | 216 (4.63), 300 (4.32), 436 (3.94) |
| 70 ml of dioxane | 25 g | 30 g of N-(2,3-dimethylbenzyl)-piperazine | 167–168° C | 219 (4.64), 280 (4.25), 298 (4.29), 434 (3.88) |
| 70 ml of dioxane | 25 g | 30 g of N-(p-tert.butylbenzyl)-piperazine | 173–174° C | 220 (4.66), 298 (4.30), 433 (3.90) |

MANUFACTURE

The stated amount of amine is added to a solution of the stated amount of rifamycin S in the stated amount of dioxane and the mixture is left to stand at room temperature until the initially violet-blue colour of the reaction mixture has changed to orange-red. Water is then added and the mixture is acidified with citric acid. The desired reaction product is taken up in chloroform. After drying and evaporating the chloroform solution, the residue which remains is dissolved in a little methanol and concentrated aqueous ascorbic acid solution is added dropwise until the initially dark coloration of the methanol solution has changed to golden yellow. After brief standing, the desired product crystallises and is obtained completely pure after two recrystallisations from chloroform-methanol-water. For melting points, see the table. The mother liquor from the first recrystallisation contains almost exclusively rifamycin SV alongside the desired reaction product.

The substituted piperazines which figure as starting materials in the table can in general be obtained by reaction of the particular alkyl bromides with piperazine in a manner which is in itself known.

In some cases it is advisable to use, instead of a bromide, the corresponding tosylate; thus, for example, N-(neopentyl)-piperazine mentioned above can be obtained by reaction of piperazine with neopentyl tosylate.

What we claim is:

1. A member selected from the group consisting of a 3-amino rifamycin SV, a 3-amino-16,17; 18,19-tetrahydro-rifamycin SV, a 3-amino-16,17; 18,19; 28,29-hexahydro-rifamycin SV, the corresponding quinonic forms of these compounds derived from rifamycin S, alkali metal salts of the hydroquinonic form of these compounds, therapeutically acceptable acid addition salts, and quarternary ammonium salts with hydrohalic, sulphuric or sulphonic acid esters of alkanols having from 1 to 16 C atoms, of these compounds, wherein the 3-amino group is a member selected from the group consisting of a 1-piperazinyl group of the formula

and of such group alkylated by lower alkyl radicals at any of the carbon atoms of the piperazine ring, wherein R is a member selected from the group consisting of
A. Hydrogen
B. a hydrocarbon radical selected from the group consisting of
  1.
    a. an unsubstituted alkyl group having not more than 6 C atoms or an alkyl group having such number of C-atoms substituted by
      a'. one or two groups selected from the group consisting of hydroxy groups, lower alkoxy groups, carbo-lower alkoxy groups, or
      b'. by one group selected from the group consisting of phenyl and phenyl substituted by one or two identical or different radicals selected from the group consisting of lower alkyl, lower alkoxy and halogen atoms
    b. phenyl and phenyl substituted by one or two identical or different radicals selected from the group consisting of lower alkyl, lower alkoxy and halogen atoms, the terms "lower" as referred to alkyl, alkoxy and carbo-lower alkoxy groups having the meaning "from 1 to 6 C-atoms",
  2. a hydrocarbon radical with not more than 35 C atoms of the formula

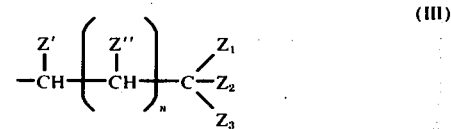

in which
$n=0$ or 1, and
$Z_1$ represents, when taken alone,
  a. an unsubstituted lower alkyl or lower alkenyl group
  b. a lower alkyl or lower alkenyl group substituted by
    a'. phenyl or phenyl substituted by 1 to 3 lower alkyl groups or halogen atoms or
    b'. $C_3$–$C_8$ cycloalkyl or $C_3$–$C_8$ cycloalkenyl
  c. phenyl or phenyl substituted by 1 to 3 lower alkyl groups or halogen atoms
  d. $C_3$–$C_8$ cycloalkyl or $C_3$–$C_8$ cycloalkenyl
$Z_2$ represents, when taken alone, hydrogen, or a lower alkyl or lower alkenyl group,
$Z_3$ represents, when taken alone, a lower alkyl or lower alkenyl group,
$Z'$ and $Z''$, when taken alone, each represent hydrogen or an alkyl group of 1–4 carbon atoms,
$Z_3$ taken together with $Z''$ represents a double bond,
$Z_2$ taken together with $Z_3$ represents a lower alkylidene or lower alkenylidene group,
$Z_1$ taken together with $Z_3$ represents an unsubstituted lower alkylene or lower alkenylene group,
$Z_1$ taken together with $Z_2$ represents an lower alkylene or lower alkenylene group in the case that $Z_3$ taken together with $Z''$ represents a double bond,
with the proviso that the cycloaliphatic groups mentioned, or those formed by an alkylene or alkenylene group $Z_1 + Z_3$ or $Z_1 + Z_2$ together with the C atom indicated in formula (III) to which $Z_1$, $Z_2$ and $Z_3$ are bonded, include such having unsubstituted cycloaliphatic rings as well as such whose rings are substituted by alkyl groups having 1 to 4 C atoms, and such in which two non-adjacent C atoms of the ring are bonded to one another directly or through an alkylidene or alkylene group having 1–4 C atoms and such in which another cycloaliphatic ring having from 3 to 5 C atoms is spirocyclically attached to one C atom of the ring, with the proviso that all such cycloaliphatic groups have not more than a total of 12 carbon atoms and from 3 to 8 ring carbon atoms, any lower alkyl, alkenyl, alkylidene or alkenylidene group containing from 1 to 7 carbon atoms,
  3. the allyl group.

2. Compounds according to claim 1, characterised in that the group R has one of the following formulae:

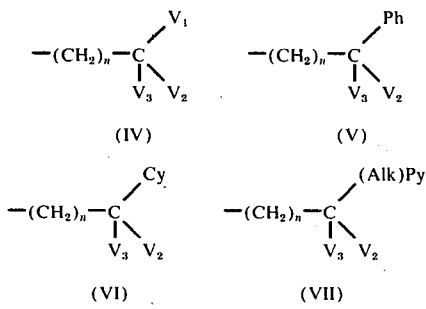

wherein $n = 1$ or 2 and $V_1$ and $V_2$, when taken alone, each denote an alkyl or alkenyl group of 1 to 7 carbon atoms, $V_3$ denotes hydrogen or an alkyl or alkenyl group of 1 to 7 carbon atoms or when taken together with $V_2$ denotes an alkylidene or alkenylidene group of 1 to 7 carbon atoms, Ph denotes an unsubstituted phenyl group or a phenyl group substituted by one or two identical or different radicals selected from the group consisting of chlorine and bromine atoms and methyl groups, Cy denotes an unsubstituted cycloalkyl or cycloalkenyl group of 5 to 8 ring carbon atoms, or such groups substituted in the ring by 1 to 3 lower alkyl groups of 1 to 4 carbon atoms, Py denotes an unsubstituted cycloalkyl or cycloalkenyl group of 5 to 8 ring carbon atoms, or such groups substituted in the ring by 1 to 3 lower alkyl groups of 1 to 4 carbon atoms, or an unsubstituted phenyl group or a phenyl group substituted by one or two identical or different radicals selected from groups consisting of chlorine, bromine and methyl groups, and Alk denotes a straight-chain or branched alkylene group of 2 to 4 carbon atoms or an alkylidene group of 1 to 4 carbon atoms.

3. Compounds according to claim 1, characterised in that the group R is a member selected from the group consisting of a radical of the following formula

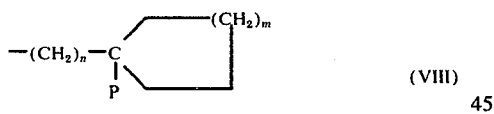

wherein $n = 1$ or 2 and $m = 1-4$, P = H or lower alkyl of 1 to 4 carbon atoms, such radical substituted in the ring by one to three identical or different lower alkyl or alkenyl groups of 1 to 4 carbon atoms, and derivatives of one of these radicals which have 1 or 2 double bonds in the cycloaliphatic ring, and derivatives of these radicals having a bridged cycloaliphatic ring, said bridge being a C-C bond or a lower alkylidene or alkylene group of 1-4 C-atoms.

4. A compound as claimed in claim 1 which is the 3-(4-isobutyl-1-piperazinyl)-rifamycin S and SV.

5. A compound as claimed in claim 1 which is the 3-(4-cyclohexylmethyl-1-piperazinyl)-refamycin S and SV.

6. A compound as claimed in claim 1 which is a member selected from the group consisting of
3-[4-(2-ethylbutyl)-1-piperazinyl]-rifamycin SV,
3-[4-(2-methylbutyl)-1-piperazinyl]-rifamycin SV,
3-(4-methallyl-1-piperazinyl)-rifamycin SV,
3-(4-allyl-1-piperazinyl)-refamycin SV,
3[4-(2-methyl-2-pentenyl)-1-piperazinyl]-rifamycin SV,
3-[4-(2-ethyl-2-butenyl)-1-piperazinyl]-rifamycin SV,
3-[4-(2-ethyl-2-hexenyl)-1-piperazinyl]-rifamycin SV,
3[4-(2,3-dimethyl-2-butenyl)-1-piperazinyl]-rifamycin SV,
3-[4-(2-ethylbutyl)-1-piperazinyl]-rifamycin SV,
3-[4-(1,2-dimethylpropyl)-1-piperazinyl]-rifamycin SV,
3-[4-(2-methylpentyl)-1-piperazinyl]-rifamycin SV,
3-[4-(3-methylpentyl)-1-piperazinyl]-rifamycin SV,
3-(4-neopentyl-1-piperazinyl)-rifamycin SV,
3-[4-(3,3-dimethylbutyl)-1-piperazinyl]-rifamycin SV
and their corresponding quinonic form compounds.

7. A compound as claimed in claim 1 which is a member selected from the group consisting of
3-(4-cyclopropylmethyl-1-piperazinyl)-rifamycin SV
3(4-cyclobutylmethyl-1-piperazinyl)-rifamycin SV
3-(4-cyclopentylmethyl-1-piperazinyl)-refamycin SV
3-[4-(2-phenylpropyl)-1-piperazinyl]-rifamycin SV
3-(4-cycloheptylmethyl-1-piperazinyl)-rifamycin SV
3-[4-(3-cyclohexen-1-yl)-methyl]-1-piperazinyl]-rifamcyin SV
3-[4-(2-norbornylmethyl)-1-piperazinyl]-rifamycin SV
3-(4-cyclooctylmethyl-1-piperazinyl)-rifamycin SV
3-[4-(4-methylcyclohexyl-methyl)-1-piperazinyl]-rifamycin SV
3-[4-(2-benzyl-propyl)-1-piperazinyl]-rifamycin SV
3-[4-(3-phenyl-2-propenyl)-1-piperazinyl]-rifamycin SV
and their corresponding quinonic form compounds.

8. A compound as claimed in claim 1, wherein the compound is a member selected from the group consisting of
3-(N-phenyl-1-piperazinyl)-rifamycin S or SV
3-(N-benzyl-1-piperazinyl)-rifamycin S or SV
3-[N-(p-chlorobenzyl)-1-piperazinyl]-rifamycin S or SV
3-(N-phenetyl-1-piperazinyl)-rifamycin S or SV
3-[N-(p-methoxy-1-piperazinyl]-rifamycin S or SV
3-[N-(p-methylbenzyl)-1-piperazinyl]-rifamycin S or SV
3-[N-(o-methylbenzyl)-1-piperazinyl]-rifamycin S or SV
3-[N-(p-isopropylbenzyl-1-piperazinyl]-rifamycin S or SV
3-[N-(m-methylbenzyl)-1-piperazinyl]-rifamycin S or SV
3-[N-(p-tert.butylbenzyl)-1-piperazinyl]-rifamycin S or SV
3-[-(2,3-dimethylbenzyl)-1-piperazinyl]-rifamycin S or SV.

9. A compound as claimed in claim 1 which is the 3-(4-methyl-1-piperazinyl)-rifamycin S or SV.

10. A compound as claimed in claim 1 which is the 3-(4-ethyl-1-piperazinyl)-rifamycin S or SV.

* * * * *

UNITED STATES PATENT AND TRADEMARK OFFICE
CERTIFICATE OF CORRECTION

PATENT NO. : 4,005,077
DATED : January 25, 1977
INVENTOR(S) : Hans Bickel and Wilhelm Kump It is certified that error appears in the above-identified patent and that said Letters Patent are hereby corrected as shown below:

Cover page under [30] Foreign Application Priority Data reads
"Aug. 24, 1965 Switzerland..........11879/65
 Aug. 11, 1969 Switzerland..........12131/69
 Dec. 8, 1969  Switzerland..........18249/69"

should be
--Aug. 24, 1965 Switzerland..........11879/65
  Aug. 11, 1969 Switzerland..........12131/69
  Dec. 8, 1969  Switzerland..........18249/69
  Sept. 28, 1973 Switzerland.........13964/73
  Sept. 28, 1973 Switzerland.........13966/73
  Jul. 26, 1974 Switzerland..........10314/74--.

Signed and Sealed this

Eleventh Day of November 1980

[SEAL]

Attest:

SIDNEY A. DIAMOND

Attesting Officer

Commissioner of Patents and Trademarks